(12) United States Patent
Purdy et al.

(10) Patent No.: US 11,116,570 B2
(45) Date of Patent: Sep. 14, 2021

(54) TUMOR ABLATION DEVICES AND RELATED METHODS

(71) Applicant: DFine, Inc., South Jordan, UT (US)

(72) Inventors: Craig Purdy, Sunnyvale, CA (US); Dan Balbierz, Redwood City, CA (US)

(73) Assignee: DFine, Inc., South Jordan, UT (US)

( * ) Notice: Subject to any disclaimer, the term of this patent is extended or adjusted under 35 U.S.C. 154(b) by 225 days.

(21) Appl. No.: 15/822,944

(22) Filed: Nov. 27, 2017

(65) Prior Publication Data

US 2018/0147007 A1 May 31, 2018

Related U.S. Application Data

(60) Provisional application No. 62/426,825, filed on Nov. 28, 2016, provisional application No. 62/426,816, filed on Nov. 28, 2016.

(51) Int. Cl.
*A61B 18/00* (2006.01)
*A61B 18/14* (2006.01)
(Continued)

(52) U.S. Cl.
CPC ........ *A61B 18/1492* (2013.01); *A61B 18/082* (2013.01); *A61B 18/10* (2013.01); *A61B 18/149* (2013.01); *A61B 18/1477* (2013.01); *A61B 18/148* (2013.01); *A61B 18/28* (2013.01); *A61B 2018/0066* (2013.01); *A61B 2018/00339* (2013.01); *A61B 2018/00565* (2013.01); *A61B 2018/00577* (2013.01); *A61B 2018/00708* (2013.01); *A61B 2018/00791* (2013.01);
(Continued)

(58) Field of Classification Search
CPC .............. A61B 2018/0057; A61B 2018/00565
See application file for complete search history.

(56) References Cited

U.S. PATENT DOCUMENTS

| 2,688,329 A | 9/1954 | Wallace |
| 3,140,623 A | 7/1964 | Hoose |
(Continued)

FOREIGN PATENT DOCUMENTS

| CA | 2785207 | 7/2011 |
| CN | 88203061 | 11/1988 |
(Continued)

OTHER PUBLICATIONS

US 7,063,700 B2, 06/2006, Michelson (withdrawn)
(Continued)

*Primary Examiner* — Linda C Dvorak
*Assistant Examiner* — Annabeth E Rodriguez
(74) *Attorney, Agent, or Firm* — Stoel Rives LLP

(57) ABSTRACT

Spinal tumor ablation devices and related systems and methods are disclosed. Some spinal tumor ablation devices include electrodes that are fixedly offset from one another. Some spinal tumor ablation devices include a thermal energy delivery probe that has at least one temperature sensor coupled thereto. The position of the at least one temperature sensor relative to other components of the spinal tumor ablation device may be controlled by adjusting the position of the thermal energy delivery probe in some spinal tumor ablation devices. Some spinal tumor ablation devices are configured to facilitate the delivery of a cement through a utility channel of the device.

11 Claims, 18 Drawing Sheets

(51) Int. Cl.
*A61B 18/08* (2006.01)
*A61B 18/10* (2006.01)
*A61B 18/28* (2006.01)

(52) U.S. Cl.
CPC .............. *A61B 2018/00797* (2013.01); *A61B 2018/00821* (2013.01); *A61B 2018/1465* (2013.01)

(56) References Cited

U.S. PATENT DOCUMENTS

| | | |
|---|---|---|
| 3,228,400 A | 1/1966 | Armao |
| 3,503,385 A | 3/1970 | Stevens |
| 3,625,200 A | 12/1971 | Muller |
| 3,664,344 A | 5/1972 | Bryne |
| 3,692,465 A | 9/1972 | Cohn et al. |
| 3,794,039 A | 2/1974 | Kollner et al. |
| 3,908,637 A | 9/1975 | Doroshow |
| 4,033,331 A | 7/1977 | Guss et al. |
| 4,131,597 A | 12/1978 | Bluethgen et al. |
| 4,236,520 A | 12/1980 | Anderson |
| 4,276,880 A | 7/1981 | Malmin |
| 4,294,251 A | 10/1981 | Grennwald et al. |
| 4,337,773 A | 7/1982 | Raftopoulos et al. |
| 4,386,717 A | 6/1983 | Koob |
| 4,399,814 A | 8/1983 | Pratt, Jr. et al. |
| 4,411,266 A | 10/1983 | Cosman |
| 4,456,017 A | 6/1984 | Miles |
| 4,473,077 A | 9/1984 | Noiles |
| 4,476,861 A | 10/1984 | Dimakos et al. |
| 4,578,061 A | 3/1986 | Lemelson |
| 4,586,923 A | 5/1986 | Gould et al. |
| 4,595,006 A | 6/1986 | Burke et al. |
| 4,619,263 A | 10/1986 | Frisbie et al. |
| 4,627,434 A | 12/1986 | Murray |
| 4,641,654 A | 2/1987 | Samson et al. |
| 4,653,489 A | 3/1987 | Tronzo |
| 4,668,295 A | 5/1987 | Bajpai |
| 4,719,968 A | 1/1988 | Speros |
| 4,722,948 A | 2/1988 | Sanderson |
| 4,731,054 A | 3/1988 | Billeter et al. |
| 4,742,817 A | 5/1988 | Kawashima et al. |
| 4,747,840 A | 5/1988 | Ladika et al. |
| 4,748,969 A | 6/1988 | Wardle |
| 4,784,638 A | 11/1988 | Ghajar et al. |
| 4,795,602 A | 1/1989 | Pretchel et al. |
| 4,842,603 A | 6/1989 | Draenert |
| 4,843,112 A | 6/1989 | Gerhart et al. |
| 4,846,814 A | 7/1989 | Ruiz |
| 4,865,586 A | 9/1989 | Hedberg |
| 4,869,906 A | 9/1989 | Dingeldein et al. |
| 4,888,366 A | 12/1989 | Chu et al. |
| 4,900,303 A | 2/1990 | Lemelson |
| 4,961,730 A | 10/1990 | Bodicky et al. |
| 4,961,731 A | 10/1990 | Bodicky |
| 4,963,151 A | 10/1990 | Ducheyene et al. |
| 4,969,870 A | 11/1990 | Kramer et al. |
| 4,969,888 A | 11/1990 | Scholten et al. |
| 4,982,730 A | 1/1991 | Royce |
| 4,998,923 A | 3/1991 | Samson et al. |
| 5,004,501 A | 4/1991 | Faccioli |
| 5,017,627 A | 5/1991 | Bonfield et al. |
| 5,046,513 A | 9/1991 | O'Leary et al. |
| 5,049,137 A | 9/1991 | Thompson |
| 5,049,157 A | 9/1991 | Mittelmeier et al. |
| 5,059,193 A | 10/1991 | Kuslich |
| 5,085,861 A | 2/1992 | Gerhart et al. |
| 5,088,991 A | 2/1992 | Weldon |
| 5,116,305 A | 2/1992 | Milder et al. |
| 5,092,891 A | 3/1992 | Kummer et al. |
| 5,103,804 A | 4/1992 | Abele |
| 5,106,381 A | 4/1992 | Chikama |
| 5,108,404 A | 4/1992 | Scholten et al. |
| 5,112,303 A | 5/1992 | Pudenz et al. |
| 5,114,414 A | 5/1992 | Buchbinder |
| 5,147,334 A | 9/1992 | Moss |
| 5,156,606 A | 10/1992 | Chin |
| 5,163,431 A | 11/1992 | Greip |
| 5,184,757 A | 2/1993 | Giannuzzi |
| 5,188,619 A | 2/1993 | Myers |
| 5,196,201 A | 3/1993 | Larsson et al. |
| 5,197,971 A | 3/1993 | Bonutti |
| 5,211,631 A | 5/1993 | Sheaff |
| 5,231,989 A | 8/1993 | Middleman et al. |
| 5,242,082 A | 9/1993 | Giannuzzi |
| 5,264,214 A | 11/1993 | Rhee et al. |
| 5,266,248 A | 11/1993 | Ohtsuka et al. |
| 5,269,750 A | 12/1993 | Grulke et al. |
| 5,282,821 A | 2/1994 | Donahue |
| 5,284,128 A | 2/1994 | Hart |
| 5,285,795 A | 2/1994 | Ryan et al. |
| 5,295,980 A | 3/1994 | Ersek |
| 5,296,026 A | 3/1994 | Monroe et al. |
| 5,308,342 A | 5/1994 | Sepetka et al. |
| 5,322,064 A | 6/1994 | Lundquist |
| 5,322,505 A | 6/1994 | Krause et al. |
| 5,334,181 A | 8/1994 | Rubinsky et al. |
| 5,336,699 A | 8/1994 | Cooke et al. |
| 5,343,877 A | 9/1994 | Park |
| 5,352,715 A | 10/1994 | Wallace et al. |
| 5,356,629 A | 10/1994 | Sander |
| 5,360,416 A | 11/1994 | Ausherman et al. |
| 5,368,598 A | 11/1994 | Hasson |
| 5,372,587 A | 12/1994 | Hammerslag et al. |
| 5,378,234 A | 1/1995 | Hammerslag et al. |
| 5,380,307 A | 1/1995 | Chee et al. |
| 5,385,563 A | 1/1995 | Groos |
| 5,389,073 A | 2/1995 | Imran |
| 5,425,770 A | 6/1995 | Piez et al. |
| 5,431,168 A | 7/1995 | Webster, Jr. |
| 5,431,639 A | 7/1995 | Shaw |
| 5,437,636 A | 8/1995 | Snoke et al. |
| 5,449,301 A | 9/1995 | Hanna et al. |
| 5,449,351 A | 9/1995 | Zohmann |
| 5,458,597 A | 10/1995 | Edwards et al. |
| 5,480,382 A | 1/1996 | Hammerslag et al. |
| 5,484,424 A | 1/1996 | Cottenceau et al. |
| 5,489,275 A | 2/1996 | Thompson et al. |
| 5,496,330 A | 3/1996 | Bates et al. |
| 5,512,610 A | 4/1996 | Lin |
| 5,514,130 A | 5/1996 | Baker |
| 5,514,137 A | 5/1996 | Coutts |
| 5,531,715 A | 7/1996 | Engelson et al. |
| 5,535,922 A | 7/1996 | Maziarz |
| 5,549,542 A | 8/1996 | Kovalcheck |
| 5,549,679 A | 8/1996 | Kuslich |
| 5,554,114 A | 9/1996 | Wallace et al. |
| 5,571,085 A | 11/1996 | Accisano, III |
| 5,571,088 A | 11/1996 | Lennox |
| 5,574,075 A | 11/1996 | Draemert |
| 5,599,346 A | 2/1997 | Edwards et al. |
| 5,616,121 A | 4/1997 | McKay |
| 5,620,447 A | 4/1997 | Smith et al. |
| 5,620,467 A | 4/1997 | Wagner |
| 5,624,396 A | 4/1997 | McNamara et al. |
| 5,628,771 A | 5/1997 | Mizukawa et al. |
| 5,637,090 A | 6/1997 | McGee |
| 5,637,091 A | 6/1997 | Hakky et al. |
| 5,662,680 A | 9/1997 | Desai |
| 5,681,282 A | 10/1997 | Eggers et al. |
| 5,681,289 A | 10/1997 | Wilcox et al. |
| 5,681,317 A | 10/1997 | Caldarise |
| 5,685,826 A | 11/1997 | Bonutti |
| 5,695,513 A | 12/1997 | Johnson et al. |
| 5,697,536 A | 12/1997 | Eggers et al. |
| 5,697,909 A | 12/1997 | Eggers et al. |
| 5,700,157 A | 12/1997 | Chung |
| 5,704,926 A | 1/1998 | Sutton |
| 5,709,697 A | 1/1998 | Ratcliff et al. |
| 5,725,568 A | 3/1998 | Hastings |
| 5,735,829 A | 4/1998 | Cherian |
| 5,741,320 A | 4/1998 | Thornton et al. |
| 5,766,153 A | 6/1998 | Eggers et al. |
| 5,800,408 A | 9/1998 | Strauss et al. |

(56) References Cited

U.S. PATENT DOCUMENTS

| | | | |
|---|---|---|---|
| 5,810,804 | A | 9/1998 | Gough |
| 5,810,867 | A | 9/1998 | Zarbatany et al. |
| 5,820,592 | A | 10/1998 | Hammerslag et al. |
| 5,833,632 | A | 11/1998 | Jacobsen et al. |
| 5,833,692 | A | 11/1998 | Cesarini et al. |
| 5,847,046 | A | 12/1998 | Jiang et al. |
| 5,849,028 | A | 12/1998 | Chen |
| 5,851,212 | A | 12/1998 | Zirps et al. |
| 5,855,577 | A | 1/1999 | Murphy-Chutorian et al. |
| 5,858,003 | A | 1/1999 | Atala |
| 5,860,952 | A | 1/1999 | Quinn |
| 5,860,974 | A | 1/1999 | Abele |
| 5,876,373 | A | 3/1999 | Giba et al. |
| 5,891,027 | A | 4/1999 | Tu |
| 5,902,251 | A | 5/1999 | Vanhooydonk |
| 5,902,839 | A | 5/1999 | Lautenschlager et al. |
| 5,914,356 | A | 6/1999 | Erbe |
| 5,921,956 | A | 7/1999 | Grinberg et al. |
| 5,928,239 | A | 7/1999 | Mirza |
| 5,931,829 | A | 8/1999 | Burbank et al. |
| 5,944,715 | A | 8/1999 | Goble et al. |
| 5,947,964 | A | 9/1999 | Eggers |
| 5,972,015 | A | 10/1999 | Scribner et al. |
| 5,997,581 | A | 12/1999 | Khalili |
| 6,019,765 | A | 2/2000 | Thornhill et al. |
| 6,027,487 | A | 2/2000 | Crocker |
| 6,030,360 | A | 2/2000 | Biggs |
| 6,048,346 | A | 4/2000 | Reiley et al. |
| 6,059,739 | A | 5/2000 | Baumann |
| 6,063,078 | A | 5/2000 | Wittkampf |
| 6,064,902 | A | 5/2000 | Haissaguerre |
| 6,066,154 | A | 5/2000 | Reiley et al. |
| 6,066,176 | A | 5/2000 | Oshida |
| 6,073,051 | A | 6/2000 | Sharkey et al. |
| 6,080,801 | A | 6/2000 | Draenert et al. |
| 6,099,514 | A | 8/2000 | Sharkey et al. |
| 6,106,524 | A | 8/2000 | Eggers et al. |
| 6,106,539 | A | 8/2000 | Fortier |
| 6,110,155 | A | 8/2000 | Baudino |
| 6,123,702 | A | 9/2000 | Swanson |
| 6,127,597 | A | 10/2000 | Beyar et al. |
| 6,135,999 | A | 10/2000 | Fanton et al. |
| 6,146,355 | A | 11/2000 | Biggs |
| 6,156,254 | A | 12/2000 | Andrews et al. |
| 6,183,435 | B1 | 2/2001 | Bumbalough et al. |
| 6,203,507 | B1 | 3/2001 | Wadsworth et al. |
| 6,203,574 | B1 | 3/2001 | Kawamura |
| 6,228,052 | B1 | 5/2001 | Pohndorf |
| 6,228,904 | B1 | 5/2001 | Yadav et al. |
| 6,231,569 | B1 | 5/2001 | Bek et al. |
| 6,231,615 | B1 | 5/2001 | Preissman |
| 6,235,043 | B1 | 5/2001 | Reiley et al. |
| 6,241,734 | B1 | 6/2001 | Scribner et al. |
| 6,248,110 | B1 | 6/2001 | Reiley et al. |
| 6,251,092 | B1 | 6/2001 | Qin et al. |
| 6,258,086 | B1 | 7/2001 | Ashley et al. |
| 6,270,476 | B1 | 8/2001 | Santoianni et al. |
| 6,280,413 | B1 | 8/2001 | Clark et al. |
| 6,280,434 | B1 | 8/2001 | Kinoshita et al. |
| 6,280,441 | B1 | 8/2001 | Ryan |
| 6,280,456 | B1 | 8/2001 | Scribner et al. |
| 6,280,473 | B1 | 8/2001 | Lemperle et al. |
| 6,283,960 | B1 | 9/2001 | Ashley |
| 6,291,547 | B1 | 9/2001 | Lyles |
| 6,312,428 | B1 | 11/2001 | Eggers |
| 6,312,454 | B1 | 11/2001 | Stockel et al. |
| 6,332,894 | B1 | 12/2001 | Stalcup et al. |
| 6,348,055 | B1 | 2/2002 | Preissman |
| 6,352,533 | B1 | 3/2002 | Ellman et al. |
| 6,358,251 | B1 | 3/2002 | Mirza |
| 6,375,659 | B1 | 4/2002 | Erbe et al. |
| 6,383,188 | B2 | 5/2002 | Kuslich et al. |
| 6,383,190 | B1 | 5/2002 | Preissman |
| 6,395,007 | B1 | 5/2002 | Bhatnagar et al. |
| 6,408,889 | B1 | 6/2002 | Komachi |
| 6,409,722 | B1 | 6/2002 | Hoey et al. |
| 6,428,894 | B1 | 8/2002 | Babich et al. |
| 6,437,019 | B1 | 8/2002 | Rusin et al. |
| 6,440,138 | B1 | 8/2002 | Reiley et al. |
| 6,447,506 | B1 | 9/2002 | Swanson et al. |
| 6,447,514 | B1 | 9/2002 | Stalcup et al. |
| 6,464,683 | B1 | 10/2002 | Samuelson et al. |
| 6,478,793 | B1 * | 11/2002 | Cosman ............ A61B 18/1477 128/898 |
| 6,479,565 | B1 | 11/2002 | Stanley |
| 6,484,904 | B1 | 11/2002 | Horner et al. |
| 6,506,217 | B1 | 1/2003 | Arnett |
| 6,511,471 | B2 | 1/2003 | Rosenman et al. |
| 6,524,296 | B1 | 2/2003 | Beals |
| 6,565,588 | B1 | 5/2003 | Clement et al. |
| 6,575,969 | B1 * | 6/2003 | Rittman, III ....... A61B 18/1482 606/41 |
| 6,575,978 | B2 | 6/2003 | Peterson et al. |
| 6,576,249 | B1 | 6/2003 | Gendler et al. |
| 6,582,446 | B1 | 6/2003 | Marchosky |
| 6,592,559 | B1 | 7/2003 | Pakter et al. |
| 6,599,961 | B1 | 7/2003 | Pienkowski et al. |
| 6,602,248 | B1 | 8/2003 | Sharps et al. |
| 6,607,544 | B1 | 8/2003 | Boucher et al. |
| 6,613,054 | B2 | 9/2003 | Scribner et al. |
| 6,620,162 | B2 | 9/2003 | Kuslich et al. |
| 6,622,731 | B2 | 9/2003 | Daniel et al. |
| 6,623,448 | B2 | 9/2003 | Slater |
| 6,638,268 | B2 | 10/2003 | Niazi |
| 6,663,647 | B2 | 10/2003 | Reiley et al. |
| 6,641,587 | B2 | 11/2003 | Scribner et al. |
| 6,645,213 | B2 | 11/2003 | Sand et al. |
| 6,676,665 | B2 | 1/2004 | Foley et al. |
| 6,679,886 | B2 | 1/2004 | Weikel et al. |
| 6,689,823 | B1 | 2/2004 | Bellare et al. |
| 6,692,532 | B1 | 2/2004 | Healy et al. |
| 6,716,216 | B1 | 4/2004 | Boucher et al. |
| 6,719,761 | B1 | 4/2004 | Reiley et al. |
| 6,719,773 | B1 | 4/2004 | Boucher et al. |
| 6,726,691 | B2 | 4/2004 | Osorio et al. |
| 6,730,095 | B2 | 5/2004 | Olson, Jr. et al. |
| 6,740,090 | B1 | 5/2004 | Cragg et al. |
| 6,740,093 | B2 | 5/2004 | Hochschuler et al. |
| 6,743,239 | B1 | 6/2004 | Kuehn et al. |
| 6,746,451 | B2 | 6/2004 | Middleton et al. |
| 6,752,863 | B2 | 6/2004 | Lyles et al. |
| 6,753,007 | B2 | 6/2004 | Haggard et al. |
| 6,770,079 | B2 | 8/2004 | Bhatnagar et al. |
| 6,814,734 | B2 | 11/2004 | Chappuis et al. |
| 6,814,736 | B2 | 11/2004 | Reiley et al. |
| 6,818,001 | B2 | 11/2004 | Wulfman et al. |
| 6,832,984 | B2 | 12/2004 | Stelzer et al. |
| 6,835,193 | B2 | 12/2004 | Epstein et al. |
| 6,837,867 | B2 | 1/2005 | Kortelling |
| 6,863,672 | B2 | 3/2005 | Reiley et al. |
| 6,869,430 | B2 | 3/2005 | Balbierz et al. |
| 6,869,445 | B1 | 3/2005 | Johnson |
| 6,875,219 | B2 | 4/2005 | Arramon |
| 6,881,214 | B2 | 4/2005 | Cosman et al. |
| 6,887,246 | B2 | 5/2005 | Bhatnagar et al. |
| 6,899,715 | B1 | 5/2005 | Beaty |
| 6,899,719 | B2 | 5/2005 | Reiley et al. |
| 6,907,884 | B2 | 6/2005 | Pellegrao et al. |
| 6,913,594 | B2 | 7/2005 | Coleman et al. |
| 6,916,306 | B1 | 7/2005 | Jenkins et al. |
| 6,923,813 | B2 | 8/2005 | Phillips |
| 6,945,956 | B2 | 9/2005 | Waldhauser et al. |
| 6,953,594 | B2 | 10/2005 | Lee et al. |
| 6,955,716 | B2 | 10/2005 | Xu et al. |
| 6,976,987 | B2 | 12/2005 | Flores |
| 6,979,312 | B2 | 12/2005 | Shimada |
| 6,979,352 | B2 | 12/2005 | Reynolds |
| 6,981,981 | B2 | 1/2006 | Reiley et al. |
| 6,991,616 | B2 | 1/2006 | Bencini et al. |
| 6,998,128 | B2 | 2/2006 | Haggard et al. |
| 7,004,930 | B2 | 2/2006 | Marshall |
| 7,004,945 | B2 | 3/2006 | Boyd et al. |
| 7,008,433 | B2 | 3/2006 | Voellmicke et al. |
| 7,018,460 | B2 | 3/2006 | Xu et al. |

(56) References Cited

U.S. PATENT DOCUMENTS

| | | |
|---|---|---|
| 7,022,133 B2 | 4/2006 | Yee et al. |
| 7,029,468 B2 | 4/2006 | Honebrink |
| 7,044,954 B2 | 5/2006 | Reiley et al. |
| 7,059,330 B1 | 6/2006 | Makower et al. |
| 7,063,682 B1 | 6/2006 | Whayne et al. |
| 7,066,942 B2 | 6/2006 | Treace |
| RE39,196 E | 7/2006 | Ying et al. |
| 7,081,122 B1 | 7/2006 | Reiley et al. |
| 7,081,161 B2 | 7/2006 | Genge et al. |
| 7,091,258 B2 | 8/2006 | Neubert et al. |
| 7,091,260 B2 | 8/2006 | Kühn |
| 7,094,202 B2 | 8/2006 | Nobis et al. |
| 7,094,286 B2 | 8/2006 | Liu |
| 7,108,696 B2 | 9/2006 | Daniel et al. |
| 7,109,254 B2 | 9/2006 | Müller et al. |
| 7,112,205 B2 | 9/2006 | Carrison |
| 7,114,501 B2 | 10/2006 | Johnson et al. |
| 7,138,442 B2 | 11/2006 | Smith et al. |
| 7,153,306 B2 | 12/2006 | Ralph et al. |
| 7,153,307 B2 | 12/2006 | Scribner et al. |
| 7,156,843 B2 | 1/2007 | Skarda |
| 7,156,845 B2 | 1/2007 | Mulier |
| 7,166,121 B2 | 1/2007 | Reiley et al. |
| 7,172,629 B2 | 2/2007 | McKay et al. |
| 7,179,255 B2 | 2/2007 | Lettice et al. |
| 7,186,234 B2 | 3/2007 | Dahla et al. |
| 7,186,761 B2 | 3/2007 | Soffiati et al. |
| 7,226,481 B2 | 6/2007 | Kuslich et al. |
| 7,252,671 B2 | 8/2007 | Scribner et al. |
| 7,160,296 B2 | 9/2007 | Pearson et al. |
| 7,267,683 B2 | 9/2007 | Sharkey et al. |
| 7,270,661 B2 | 9/2007 | Dahla et al. |
| 7,294,127 B2 | 11/2007 | Leung |
| 7,465,318 B2 | 12/2008 | Sennett et al. |
| 7,480,533 B2 | 1/2009 | Cosman et al. |
| 7,503,920 B2 | 3/2009 | Siegal |
| 7,544,196 B2 | 6/2009 | Bagga et al. |
| 7,569,054 B2 | 6/2009 | Michelson |
| 7,559,932 B2 | 7/2009 | Truckai et al. |
| 7,572,263 B2 | 8/2009 | Preissman |
| 7,591,822 B2 | 9/2009 | Olson, Jr. et al. |
| 7,625,364 B2 | 12/2009 | Corcoran et al. |
| 7,641,664 B2 | 1/2010 | Pagano |
| 7,731,720 B2 | 6/2010 | Sand et al. |
| 7,811,291 B2 | 10/2010 | Liu et al. |
| 7,824,403 B2 | 11/2010 | Vaska |
| 7,842,041 B2 | 11/2010 | Liu et al. |
| 7,887,543 B2 | 2/2011 | Sand et al. |
| 7,905,884 B2 | 3/2011 | Simonton et al. |
| 7,918,874 B2 | 4/2011 | Siegal |
| 7,972,340 B2 | 7/2011 | Sand et al. |
| 7,976,542 B1 | 7/2011 | Cosman |
| 8,034,071 B2 | 10/2011 | Scribner et al. |
| 8,246,627 B2 | 8/2012 | Vanleeuwen et al. |
| 8,284,128 B2 | 10/2012 | Kimura |
| 8,518,036 B2 | 8/2013 | Leung |
| 8,583,260 B2 | 11/2013 | Knudson |
| 8,591,507 B2 | 11/2013 | Kramer et al. |
| 8,663,226 B2 | 3/2014 | Germain |
| RE44,883 E | 5/2014 | Cha |
| 8,758,349 B2 | 6/2014 | Germain et al. |
| 8,827,981 B2 | 9/2014 | Liu et al. |
| 8,864,760 B2 | 10/2014 | Kramer et al. |
| 8,936,631 B2 | 1/2015 | Nguyen |
| 9,113,974 B2 | 8/2015 | Germain |
| 9,125,671 B2 | 9/2015 | Germain et al. |
| 9,161,809 B2 | 10/2015 | Germain et al. |
| 9,421,057 B2 | 8/2016 | Germain |
| 9,743,938 B2 | 8/2017 | Germain et al. |
| 2001/0011174 A1 | 8/2001 | Reiley et al. |
| 2001/0023349 A1 | 9/2001 | Van Tassel et al. |
| 2002/0007180 A1 | 1/2002 | Wittenberger et al. |
| 2002/0013600 A1 | 1/2002 | Scribner et al. |
| 2002/0026195 A1 | 2/2002 | Layne et al. |
| 2002/0026197 A1 | 2/2002 | Foley et al. |
| 2002/0068929 A1 | 6/2002 | Zvuloni |
| 2002/0068974 A1 | 6/2002 | Kuslich et al. |
| 2002/0077595 A1 | 6/2002 | Hundertmark et al. |
| 2002/0082605 A1 | 6/2002 | Reiley et al. |
| 2002/0115742 A1 | 8/2002 | Trieu et al. |
| 2002/0128638 A1 | 9/2002 | Chauvel et al. |
| 2002/0133148 A1 | 9/2002 | Daniel et al. |
| 2002/0156483 A1 | 10/2002 | Voellmicke et al. |
| 2002/0188299 A1 | 12/2002 | Reiley et al. |
| 2002/0188300 A1 | 12/2002 | Arramon et al. |
| 2003/0014094 A1 | 1/2003 | Hammack et al. |
| 2003/0032929 A1 | 2/2003 | McGuckin |
| 2003/0036763 A1 | 2/2003 | Bhatnagar et al. |
| 2003/0043963 A1 | 3/2003 | Yamagami et al. |
| 2003/0050644 A1 | 3/2003 | Boucher et al. |
| 2003/0069522 A1 | 4/2003 | Jasobsen et al. |
| 2003/0073979 A1 | 4/2003 | Naimark et al. |
| 2003/0130664 A1 | 7/2003 | Boucher et al. |
| 2003/0163085 A1 | 8/2003 | Tanner et al. |
| 2003/0171744 A1 | 9/2003 | Leung et al. |
| 2003/0191489 A1 | 10/2003 | Reiley et al. |
| 2003/0195547 A1 | 10/2003 | Scribner et al. |
| 2003/0212394 A1 | 11/2003 | Pearson et al. |
| 2003/0212395 A1 | 11/2003 | Woloszko et al. |
| 2003/0220414 A1 | 11/2003 | Axen et al. |
| 2003/0225432 A1 | 12/2003 | Baptiste et al. |
| 2003/0233096 A1 | 12/2003 | Osorio et al. |
| 2004/0023384 A1 | 2/2004 | Fukaya |
| 2004/0023784 A1 | 2/2004 | Yu et al. |
| 2004/0024081 A1 | 2/2004 | Trieu et al. |
| 2004/0024398 A1 | 2/2004 | Hovda et al. |
| 2004/0024409 A1 | 2/2004 | Sand et al. |
| 2004/0024410 A1 | 2/2004 | Olson et al. |
| 2004/0034384 A1 | 2/2004 | Fukaya |
| 2004/0044096 A1 | 3/2004 | Smith et al. |
| 2004/0044350 A1 | 3/2004 | Martin et al. |
| 2004/0059328 A1 | 3/2004 | Daniel et al. |
| 2004/0087936 A1 | 5/2004 | Stern et al. |
| 2004/0087994 A1 | 5/2004 | Suddaby |
| 2004/0092946 A1 | 5/2004 | Bagga et al. |
| 2004/0097612 A1 | 5/2004 | Rosenberg et al. |
| 2004/0111136 A1 | 6/2004 | Sharkey et al. |
| 2004/0127987 A1 | 7/2004 | Evans et al. |
| 2004/0133208 A1 | 7/2004 | Weikel et al. |
| 2004/0138758 A1 | 7/2004 | Evans et al. |
| 2004/0153064 A1 | 8/2004 | Foley et al. |
| 2004/0153115 A1 | 8/2004 | Reiley et al. |
| 2004/0158237 A1 | 8/2004 | Abboud et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0210231 A1 | 10/2004 | Boucher et al. |
| 2004/0215343 A1 | 10/2004 | Hochschuler et al. |
| 2004/0220577 A1 | 11/2004 | Cragg |
| 2004/0220680 A1 | 11/2004 | Yamamoto et al. |
| 2004/0225296 A1 | 11/2004 | Reiss et al. |
| 2004/0226479 A1 | 11/2004 | Lyles et al. |
| 2004/0230309 A1 | 11/2004 | DiMauro et al. |
| 2004/0236186 A1 | 11/2004 | Chu |
| 2004/0247644 A1 | 12/2004 | Bratt et al. |
| 2004/0267271 A9 | 12/2004 | Scribner et al. |
| 2005/0027245 A1 | 2/2005 | Sachdeva et al. |
| 2005/0033303 A1 | 2/2005 | Chappuis et al. |
| 2005/0038383 A1 | 2/2005 | Kelley et al. |
| 2005/0038422 A1 | 2/2005 | Maurice |
| 2005/0043737 A1 | 2/2005 | Relley et al. |
| 2005/0055030 A1 | 3/2005 | Falahee |
| 2005/0060030 A1 | 3/2005 | Lashinski et al. |
| 2005/0070844 A1 | 3/2005 | Chow et al. |
| 2005/0070912 A1 | 3/2005 | Voellmicke |
| 2005/0070915 A1 | 3/2005 | Mazzuca et al. |
| 2005/0090852 A1 | 4/2005 | Layne et al. |
| 2005/0113836 A1 | 5/2005 | Loier et al. |
| 2005/0119650 A1 | 6/2005 | Sanders et al. |
| 2005/0124989 A1 | 6/2005 | Suddaby |
| 2005/0143827 A1 | 6/2005 | Globerman et al. |
| 2005/0177168 A1 | 8/2005 | Brunnett et al. |
| 2005/0177210 A1 | 8/2005 | Leung et al. |
| 2005/0182412 A1 | 8/2005 | Johnson et al. |

(56) References Cited

U.S. PATENT DOCUMENTS

| | | |
|---|---|---|
| 2005/0182413 A1 | 8/2005 | Johnson et al. |
| 2005/0187556 A1 | 8/2005 | Stack et al. |
| 2005/0199156 A1 | 9/2005 | Khairoun et al. |
| 2005/0209557 A1 | 9/2005 | Carroll et al. |
| 2005/0216018 A1 | 9/2005 | Sennett |
| 2005/0228391 A1 | 10/2005 | Levy et al. |
| 2005/0234425 A1 | 10/2005 | Miller et al. |
| 2005/0240193 A1 | 10/2005 | Layne et al. |
| 2005/0251266 A1 | 11/2005 | Maspero et al. |
| 2005/0251267 A1 | 11/2005 | Winterbottom et al. |
| 2005/0261683 A1 | 11/2005 | Veldhuizen et al. |
| 2005/0283148 A1 | 12/2005 | Janssen |
| 2005/0287771 A1 | 12/2005 | Seamons et al. |
| 2006/0024348 A1 | 2/2006 | Engqvist et al. |
| 2006/0025763 A1 | 2/2006 | Nelson et al. |
| 2006/0041033 A1 | 2/2006 | Bisig et al. |
| 2006/0052743 A1 | 3/2006 | Reynolds |
| 2006/0064101 A1 | 3/2006 | Arramon |
| 2006/0074433 A1 | 4/2006 | McGill et al. |
| 2006/0084977 A1 | 4/2006 | Lieberman |
| 2006/0085009 A1 | 4/2006 | Truckai et al. |
| 2006/0100635 A1 | 5/2006 | Reiley et al. |
| 2006/0100706 A1 | 5/2006 | Shadduck et al. |
| 2006/0106392 A1 | 5/2006 | Embry |
| 2006/0106459 A1 | 5/2006 | Truckai et al. |
| 2006/0116689 A1 | 6/2006 | Albans et al. |
| 2006/0116690 A1 | 6/2006 | Pagano |
| 2006/0122623 A1 | 6/2006 | Truckai et al. |
| 2006/0142732 A1 | 6/2006 | Karmarkar et al. |
| 2006/0149268 A1 | 7/2006 | Truckai et al. |
| 2006/0149281 A1 | 7/2006 | Reiley et al. |
| 2006/0156959 A1 | 7/2006 | Engqvist et al. |
| 2006/0184106 A1 | 8/2006 | McDaniel et al. |
| 2006/0184192 A1 | 8/2006 | Markworth et al. |
| 2006/0200121 A1 | 9/2006 | Mowery |
| 2006/0206116 A1 | 9/2006 | Yeung |
| 2006/0206136 A1 | 9/2006 | Sachdeva et al. |
| 2006/0217704 A1 | 9/2006 | Cockburn et al. |
| 2006/0217736 A1 | 9/2006 | Kaneko |
| 2006/0229625 A1 | 10/2006 | Truckai et al. |
| 2006/0229631 A1 | 10/2006 | Reiley et al. |
| 2006/0235417 A1 | 10/2006 | Sala |
| 2006/0259023 A1 | 11/2006 | Abboud et al. |
| 2006/0264819 A1 | 11/2006 | Fischer et al. |
| 2006/0264945 A1 | 11/2006 | Edidin et al. |
| 2006/0266372 A1 | 11/2006 | Miller et al. |
| 2006/0270750 A1 | 11/2006 | Almen et al. |
| 2006/0271061 A1 | 11/2006 | Beyar et al. |
| 2006/0276797 A1 | 12/2006 | Botimer |
| 2006/0276819 A1 | 12/2006 | Osorio et al. |
| 2006/0293687 A1 | 12/2006 | Bogert |
| 2007/0006692 A1 | 1/2007 | Phan |
| 2007/0010845 A1 | 1/2007 | Gong et al. |
| 2007/0016130 A1 | 1/2007 | Leeflang et al. |
| 2007/0016211 A1 | 1/2007 | Botimer |
| 2007/0021769 A1 | 1/2007 | Scribner et al. |
| 2007/0043373 A1 | 2/2007 | Sala |
| 2007/0055201 A1 | 3/2007 | Seto et al. |
| 2007/0055260 A1 | 3/2007 | Cragg |
| 2007/0055266 A1 | 3/2007 | Osorio et al. |
| 2007/0055275 A1 | 3/2007 | Schaller |
| 2007/0055277 A1 | 3/2007 | Osorio et al. |
| 2007/0055278 A1 | 3/2007 | Osorio et al. |
| 2007/0055279 A1 | 3/2007 | Sand et al. |
| 2007/0055281 A1 | 3/2007 | Osorio et al. |
| 2007/0055283 A1 | 3/2007 | Scribner |
| 2007/0055284 A1 | 3/2007 | Osorio |
| 2007/0055285 A1 | 3/2007 | Osorio et al. |
| 2007/0055300 A1 | 3/2007 | Osorio et al. |
| 2007/0055382 A1 | 3/2007 | Osorio et al. |
| 2007/0059281 A1 | 3/2007 | Moseley et al. |
| 2007/0067034 A1 | 3/2007 | Chirico et al. |
| 2007/0093840 A1 | 4/2007 | Pacelli |
| 2007/0114248 A1 | 5/2007 | Kovac |
| 2007/0118142 A1 | 5/2007 | Krueger et al. |
| 2007/0118143 A1 | 5/2007 | Ralph et al. |
| 2007/0142842 A1 | 6/2007 | Krueger et al. |
| 2007/0156130 A1 | 7/2007 | Thistle |
| 2007/0162042 A1 | 7/2007 | Dunker |
| 2007/0173939 A1 | 7/2007 | Kim et al. |
| 2007/0185231 A1 | 8/2007 | Liu et al. |
| 2007/0197935 A1 | 8/2007 | Reiley |
| 2007/0198023 A1 | 8/2007 | Sand et al. |
| 2007/0203500 A1 | 8/2007 | Gordon |
| 2007/0211563 A1 | 9/2007 | Devries |
| 2007/0233146 A1 | 10/2007 | Henniges et al. |
| 2007/0260223 A1 | 11/2007 | Scheibe et al. |
| 2007/0260257 A1 | 11/2007 | Phan |
| 2007/0270876 A1 | 11/2007 | Kuo et al. |
| 2007/0276319 A1 | 11/2007 | Betts |
| 2007/0282305 A1 | 12/2007 | Goldfarb et al. |
| 2008/0004615 A1 | 1/2008 | Woloszko et al. |
| 2008/0033422 A1 | 2/2008 | Turner et al. |
| 2008/0058725 A1 | 3/2008 | Scribner et al. |
| 2008/0058821 A1 | 3/2008 | Maurer et al. |
| 2008/0058827 A1 | 3/2008 | Osorio et al. |
| 2008/0058840 A1 | 3/2008 | Albrecht |
| 2008/0065020 A1 | 3/2008 | Ralph et al. |
| 2008/0065087 A1 | 3/2008 | Osorio et al. |
| 2008/0065190 A1 | 3/2008 | Osorio et al. |
| 2008/0086142 A1 | 4/2008 | Kohm et al. |
| 2008/0140079 A1 | 6/2008 | Osorio et al. |
| 2008/0183165 A1 | 7/2008 | Buysee et al. |
| 2008/0183265 A1 | 7/2008 | Bly |
| 2008/0195112 A1 | 8/2008 | Liu et al. |
| 2008/0208255 A1 | 8/2008 | Siegal |
| 2008/0221608 A1 | 9/2008 | Betts |
| 2008/0228192 A1 | 9/2008 | Beyer et al. |
| 2008/0249481 A1 | 10/2008 | Crainich |
| 2008/0249525 A1 | 10/2008 | Lee et al. |
| 2008/0255571 A1 | 10/2008 | Truckai et al. |
| 2008/0269766 A1 | 10/2008 | Justis |
| 2008/0269796 A1 | 10/2008 | Reiley et al. |
| 2008/0287741 A1 | 11/2008 | Ostrovsky et al. |
| 2008/0294167 A1 | 11/2008 | Schumacher et al. |
| 2009/0076517 A1 | 3/2009 | Reiley et al. |
| 2009/0105775 A1 | 4/2009 | Mitchell et al. |
| 2009/0131867 A1 | 5/2009 | Liu et al. |
| 2009/0131886 A1 | 5/2009 | Liu et al. |
| 2009/0131945 A1 | 5/2009 | Liu et al. |
| 2009/0131948 A1 | 5/2009 | Liu |
| 2009/0131950 A1 | 5/2009 | Liu et al. |
| 2009/0131986 A1 | 5/2009 | Lee |
| 2009/0182427 A1 | 7/2009 | Liu et al. |
| 2009/0198243 A1 | 8/2009 | Melsheimer |
| 2009/0264862 A1 | 10/2009 | Neidert et al. |
| 2009/0264892 A1 | 10/2009 | Beyar et al. |
| 2009/0292289 A9 | 11/2009 | Sand et al. |
| 2009/0293687 A1 | 12/2009 | Nino et al. |
| 2009/0299282 A1 | 12/2009 | Lau et al. |
| 2010/0057087 A1 | 3/2010 | Cha |
| 2010/0082033 A1 | 4/2010 | Germain |
| 2010/0114184 A1 | 5/2010 | Degtyar |
| 2010/0121332 A1 | 5/2010 | Crainich et al. |
| 2010/0152724 A1 | 6/2010 | Marion et al. |
| 2010/0160922 A1 | 6/2010 | Liu et al. |
| 2010/0211076 A1* | 8/2010 | Germain ............ A61B 17/1642 606/84 |
| 2010/0274270 A1 | 10/2010 | Patel |
| 2010/0298832 A1 | 11/2010 | Lau et al. |
| 2011/0034884 A9 | 2/2011 | Pellegrino et al. |
| 2011/0098701 A1 | 4/2011 | McIntyre et al. |
| 2011/0160737 A1 | 6/2011 | Steffen et al. |
| 2011/0251615 A1 | 10/2011 | Truckai et al. |
| 2011/0295261 A1 | 12/2011 | Germain |
| 2011/0295262 A1 | 12/2011 | Germain et al. |
| 2011/0301590 A1 | 12/2011 | Podhajsky et al. |
| 2012/0065543 A1 | 3/2012 | Ireland |
| 2012/0130381 A1 | 5/2012 | Germain |
| 2012/0143298 A1* | 6/2012 | Just ............... A61B 18/1492 607/122 |
| 2012/0158004 A1 | 6/2012 | Burger et al. |
| 2012/0191095 A1 | 7/2012 | Burger et al. |
| 2012/0239049 A1 | 9/2012 | Truckai |

(56) References Cited

U.S. PATENT DOCUMENTS

| | | |
|---|---|---|
| 2012/0265186 A1 | 10/2012 | Burger et al. |
| 2012/0277582 A1 | 11/2012 | Mafi |
| 2012/0277730 A1 | 11/2012 | Salahieh |
| 2012/0330180 A1 | 12/2012 | Pellegrino et al. |
| 2012/0330301 A1 | 12/2012 | Pellegrino et al. |
| 2013/0006232 A1 | 1/2013 | Pellegrino |
| 2013/0006257 A1 | 1/2013 | Lee |
| 2013/0072941 A1 | 3/2013 | Tan-Malecki et al. |
| 2013/0041377 A1 | 4/2013 | Kuntz |
| 2013/0231654 A1 | 9/2013 | Germain |
| 2013/0237795 A1 | 9/2013 | Carr |
| 2013/0261615 A1 | 10/2013 | Kramer et al. |
| 2013/0261621 A1 | 10/2013 | Kramer et al. |
| 2013/0345709 A1 | 12/2013 | Burger et al. |
| 2014/0135779 A1 | 5/2014 | Germain |
| 2014/0163566 A1 | 6/2014 | Phan et al. |
| 2014/0236144 A1 | 8/2014 | Krueger et al. |
| 2014/0316413 A1 | 10/2014 | Burger et al. |
| 2014/0350542 A1 | 11/2014 | Kramer et al. |
| 2014/0371740 A1 | 12/2014 | Germain et al. |
| 2015/0216594 A1 | 8/2015 | Prakash |
| 2015/0265333 A1 | 9/2015 | Shin et al. |
| 2015/0297246 A1 | 10/2015 | Patel et al. |
| 2015/0313614 A1 | 11/2015 | Germain |
| 2016/0066984 A1 | 3/2016 | Janssen et al. |
| 2016/0228131 A1 | 8/2016 | Brockman et al. |
| 2016/0310193 A1 | 10/2016 | Lv et al. |
| 2016/0331443 A1 | 11/2016 | Phan et al. |
| 2017/0095291 A1 | 4/2017 | Harrington |
| 2017/0105798 A1 | 4/2017 | Allison |
| 2018/0078170 A1 | 3/2018 | Panescu et al. |
| 2018/0147006 A1* | 5/2018 | Purdy ............... A61B 18/10 |
| 2018/0147007 A1* | 5/2018 | Purdy ............... A61B 18/10 |
| 2020/0078066 A1 | 3/2020 | Purdy et al. |
| 2020/0146743 A1 | 5/2020 | Defosset et al. |
| 2020/0146744 A1 | 5/2020 | Defosset et al. |
| 2020/0390449 A1 | 12/2020 | Purdy et al. |

FOREIGN PATENT DOCUMENTS

| | | |
|---|---|---|
| CN | 2841051 | 11/2006 |
| CN | 102500036 | 6/2012 |
| DE | 20314010 | 1/2015 |
| EP | 1459691 | 9/2004 |
| EP | 1927375 | 6/2008 |
| JP | 2004242936 | 9/2004 |
| JP | 2008510530 | 4/2008 |
| JP | 2008528081 | 7/2008 |
| JP | 2008541878 | 11/2008 |
| JP | 2010063887 | 3/2010 |
| JP | 2011500156 | 1/2011 |
| JP | 2015503200 | 1/2015 |
| KR | 101342906 | 12/2013 |
| WO | 1993004634 | 3/1993 |
| WO | 1996013297 | 5/1996 |
| WO | 1996020752 | 7/1996 |
| WO | 1997003611 | 2/1997 |
| WO | 2002003870 | 1/2002 |
| WO | 2003101308 | 12/2003 |
| WO | 2005039390 | 5/2005 |
| WO | 2005122938 | 12/2005 |
| WO | 2007036815 | 4/2007 |
| WO | 2007087400 | 8/2007 |
| WO | 2008076330 | 6/2008 |
| WO | 2008084479 | 7/2008 |
| WO | 2009155319 | 12/2009 |
| WO | 2010039894 | 4/2010 |
| WO | 2010081187 | 7/2010 |
| WO | 2010135602 | 11/2010 |
| WO | 2010135606 | 11/2010 |
| WO | 2011066465 | 6/2011 |
| WO | 2011114602 | 9/2011 |
| WO | 2011137357 | 11/2011 |
| WO | 2011137377 | 11/2011 |
| WO | 2012071464 | 5/2012 |
| WO | 2013147990 | 10/2013 |
| WO | 2014093673 | 6/2014 |
| WO | 2015051070 | 4/2015 |
| WO | 2016183178 | 11/2016 |

OTHER PUBLICATIONS

Office Action dated May 17, 2010 for U.S. Appl. No. 12/261,987.
Office Action dated May 21, 2014 for U.S. Appl. No. 13/098,116.
Office Action dated May 24, 2012 for U.S. Appl. No. 12/578,455.
Office Action dated May 31, 2016 for U.S. Appl. No. 14/815,620.
Office Action dated Jun. 4, 2018 for U.S. Appl. No. 15/349,715.
Office Action dated Jun. 8, 2009 for U.S. Appl. No. 11/941,764.
Office Action dated Jun. 12, 2009 for U.S. Appl. No. 11/941,733.
Office Action dated Jun. 21, 2013 for U.S. Appl. No. 13/215,098.
Office Action dated Jun. 22, 2018 for U.S. Appl. No. 15/917,454.
Office Action dated Jun. 25, 2015 for U.S. Appl. No. 13/853,397.
Office Action dated Jun. 29, 2018 for U.S. Appl. No. 15/449,591.
Office Action dated Jul. 11, 2017 for U.S. Appl. No. 14/815,812.
Office Action dated Jul. 12, 2010 for U.S. Appl. No. 11/941,764.
Office Action dated Jul. 12, 2017 for U.S. Appl. No. 13/083,411.
Office Action dated Jul. 25, 2011 for U.S. Appl. No. 11/941,733.
Office Action dated Jul. 29, 2013 for U.S. Appl. No. 13/098,116.
Office Action dated Jul. 30, 2013 for U.S. Appl. No. 13/083,411.
Office Action dated Sep. 1, 2010 for U.S. Appl. No. 12/029,428.
Office Action dated Sep. 6, 2017 for U.S. Appl. No. 15/211,359.
Office Action dated Sep. 26, 2017 for U.S. Appl. No. 15/388,598.
Office Action dated Oct. 2, 2018 for U.S. Appl. No. 14/139,372.
Office Action dated Oct. 30, 2018 for U.S. Appl. No. 15/349,715.
Office Action dated Nov. 3, 2008 for U.S. Appl. No. 11/941,764.
Office Action dated Nov. 3, 2008 for U.S. Appl. No. 12/029,428.
Office Action dated Nov. 5, 2008 for U.S. Appl. No. 11/941,733.
Office Action dated Nov. 12, 2013 for U.S. Appl. No. 13/083,411.
Office Action dated Nov. 25, 2016 for U.S. Appl. No. 13/083,411.
Office Action dated Dec. 2, 2009 for U.S. Appl. No. 12/029,428.
Office Action dated Dec. 3, 2012 for U.S. Appl. No. 12/571,174.
Office Action dated Dec. 9, 2009 for U.S. Appl. No. 12/262,064.
Office Action dated Dec. 11, 2009 for U.S. Appl. No. 12/261,987.
Office Action dated Feb. 27, 2013 for U.S. Appl. No. 12/578,455.
Office Action dated Jul. 12, 2016 for U.S. Appl. No. 14/887,007.
Office Action dated Sep. 10, 2013 for U.S. Appl. No. 12/571,174.
U.S. Appl. No. 15/836,125, filed Dec. 8, 2017.
Disc-O-Tech confidence Cement System at http:/www.disc-o-tech.com/Articles/Article.asp?CategoryID=4&ArticleID=168 accessed, ,Dec. 3, 2007.
Dai, et al.,Bone-Particle-Impregnated Bone Cement: an in vivo weight-bearing study, Journal Biomedical Materials Search, vol. 25 ,191 ,141-156.
Hasenwinkel, et al.,"A Novel High-Viscosity, Two-Solution Acrylic Bone Cement: Effect of Chemical Composition on Properties", J. Biomed Mater. Res. vol. 47, No. 1 ,1999 ,36-45.
Klawitter, et al.,Application of Porous Ceramics for the Attachment of Load Bearing Internal Orthopedic Applications, J. Biomed. Mater. Res. Symp., 2(1) ,1972 ,61-229.
Liu, et al.,Bone-Particle-Impregnated Bone Cement: An In Vitro Study, Journal of Biomedical Materials Research, vol. 21 ,1987 ,247-261.
Park, et al.,Biomaterials: An Introduction—Second Edition, Plenum Press ,1992 ,177-178.
Park, et al.,The Materials Properties of Bone-Particle Impregnated PMMA, Journal of Biomedical Engineering, vol. 108 ,1986 ,141-148.
International Search Report and Written Opinion dated Feb. 21, 2018 for PCT/US2017/063281.
Notice of Allowance dated Aug. 8, 2019 for U.S. Appl. No. 15/836,125.
Notice of Allowance dated Aug. 9, 2019 for U.S. Appl. No. 15/836,241.
Notice of Allowance dated Sep. 20, 2019 for U.S. Appl. No. 15/793,509.
Office Action dated May 1, 2009 for U.S. Appl. No. 12/261,987.
Office Action dated May 5, 2010 for U.S. Appl. No. 11/941,764.

(56) References Cited

OTHER PUBLICATIONS

European Examination Report dated Dec. 19, 2017 for EP13767383.6.
European Search Report dated Jan. 7, 2019 for EP16793433.0.
European Search Report dated Jun. 8, 2017 for EP17154660.9.
European Search Report dated Nov. 15, 2017 for EP09818476.5.
European Search Report dated Nov. 16, 2016 for EP14772615.2.
International Search Report and Written Opinion dated Jan. 9, 2012 for PCT/US2011/034185.
International Search Report and Written Opinion dated Jan. 22, 2009 for PCT/US2008/83698.
International Search Report and Written Opinion dated Feb. 7, 2018 for PCT/US2017/058303.
International Search Report and Written Opinion dated Mar. 30, 2018 for PCT/US2017/065328.
International Search Report and Written Opinion dated Apr. 23, 2016 for PCT/US2018/012372.
International Search Report and Written Opinion dated Jul. 20, 2010 for PCT/US2010/035687.
International Search Report and Written Opinion dated Jul. 26, 2011 for PCT/US2011/034628.
International Search Report and Written Opinion dated Aug. 25, 2009 for PCT/US2009/035726.
International Search Report and Written Opinion dated Nov. 20, 2009 for PCT/US2009/059113.
Notice of Allowance dated Jan. 4, 2017 for U.S. Appl. No. 13/302,927.
Notice of Allowance dated Jan. 18, 2017 for U.S. Appl. No. 13/097,998.
Notice of Allowance dated Feb. 21, 2019 for U.S. Appl. No. 14/139,372.
Notice of Allowance dated dated Apr. 3, 2019 for U.S. Appl. No. 15/349,715.
Notice of Allowance dated Apr. 9, 2014 for U.S. Appl. No. 12/578,455.
Notice of Allowance dated Apr. 23, 2018 for U.S. Appl. No. 13/083,411.
Notice of Allowance dated May 3, 2017 for U.S. Appl. No. 14/815,620.
Notice of Allowance dated May 11, 2018 for U.S. Appl. No. 14/453,427.
Notice of Allowance dated May 26, 2015 for U.S. Appl. No. 13/098,116.
Notice of Allowance dated Aug. 24, 2018 for U.S. Appl. No. 15/388,598.
Notice of Allowance dated Oct. 28, 2016 for U.S. Appl. No. 13/853,397.
Notice of Allowance dated Nov. 8, 2013 for U.S. Appl. No. 12/578,455.
Notice of Allowance dated Nov. 9, 2017 for U.S. Appl. No. 14/815,812.
Notice of Allowance dated Nov. 18, 2016 for U.S. Appl. No. 13/097,998.
Notice of Allowance dated Nov. 25, 2013 for U.S. Appl. No. 12/571,174.
Notice of Allowance dated Nov. 25, 2016 for U.S. Appl. No. 13/853,397.
Notice of Allowance dated Dec. 13, 2018 for U.S. Appl. No. 15/917,454.
Notice of Allowance dated Dec. 28, 2017 for U.S. Appl. No. 15/211,359.
Notice of Allowance dated Aug. 31, 2016 for U.S. Appl. No. 14/887,007.
Office Action dated Jan. 18, 2017 for U.S. Appl. No. 14/815,620.
Office Action dated Jan. 26, 2011 for U.S. Appl. No. 11/941,764.
Office Action dated Jan. 26, 2017 for U.S. Appl. No. 14/815,812.
Office Action dated Feb. 3, 2016 for U.S. Appl. No. 13/853,397.
Office Action dated Feb. 10, 2015 for U.S. Appl. No. 13/083,411.
Office Action dated Feb. 23, 2010 for U.S. Appl. No. 11/941,733.
Office Action dated Feb. 23, 2010 for U.S. Appl. No. 11/941,764.
Office Action dated Mar. 1, 2017 for U.S. Appl. No. 15/211,359.
Office Action dated Mar. 21, 2011 for U.S. Appl. No. 11/941,764.
Office Action dated Mar. 21, 2011 for U.S. Appl. No. 12/029,428.
Office Action dated Apr. 19, 2018 for U.S. Appl. No. 15/388,598.
Office Action dated Apr. 24, 2017 for U.S. Appl. No. 14/453,427.
Office Action dated Apr. 26, 2010 for U.S. Appl. No. 12/029,428.
Office Action dated May 6, 2019 for U.S. Appl. No. 15/675,315.
Office Action dated May 13, 2009 for U.S. Appl. No. 12/029,428.
Office Action dated Nov. 7, 2019 for U.S. Appl. No. 15/675,315.
Office Action dated Dec. 20, 2019 for U.S. Appl. No. 15/862,441.
Office Action dated Dec. 26, 2019 for U.S. Appl. No. 15/822,864.
International Search Report and Written Opinion dated Apr. 8, 2020 for PCT/US2019060279.
Notice of Allowance dated Feb. 19, 2020 for U.S. Appl. No. 15/675,315.
International Search Report and Written Opinion dated Apr. 8, 2020 for PCT/US2019/060273.
European Search Report dated May 29, 2020 for EP17874650.9.
European Search Report dated Jun. 16, 2020 for EP17863626.2.
European Search Report dated Jul. 1, 2020 for EP17878602.6.
European Search Report dated Jul. 15, 2020 for EP18736547.3.
Office Action dated Jun. 11, 2020 for U.S. Appl. No. 15/822,864.
Notice of Allowance dated Mar. 31, 2021 for U.S. Appl. No. 15/822,864.
European Search Report dated Jul. 7, 2021 for EP16793433.0.

* cited by examiner

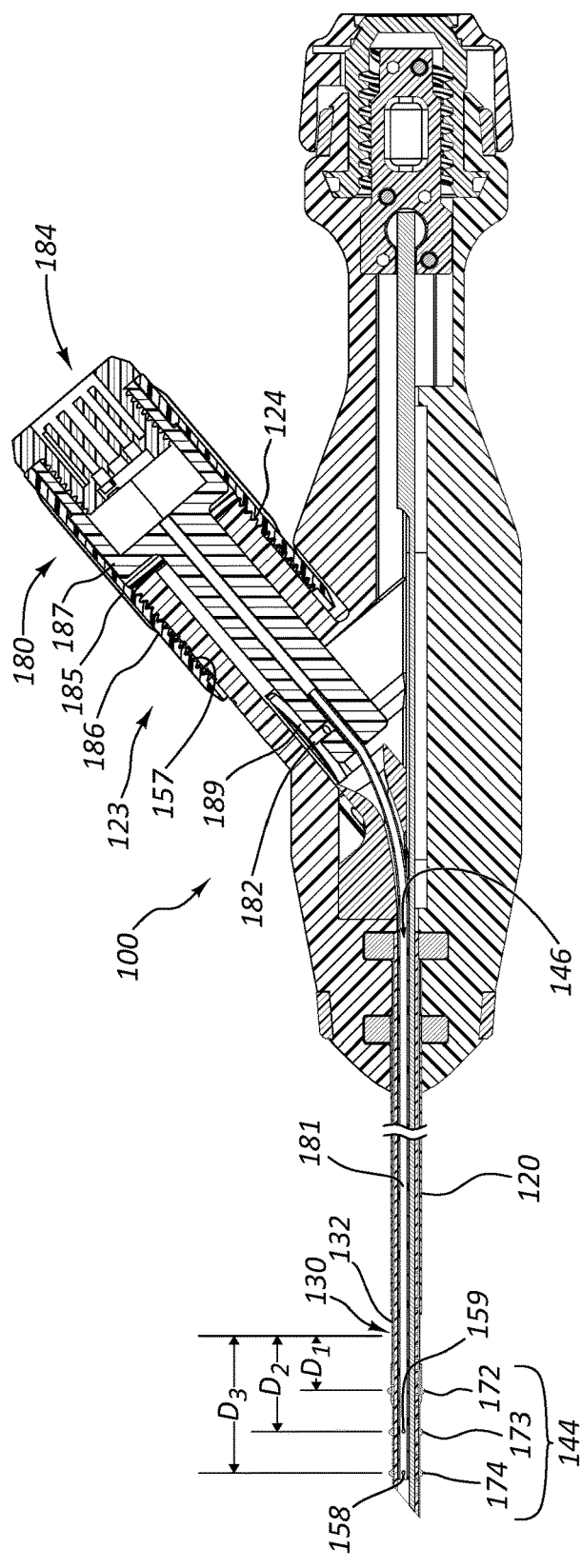
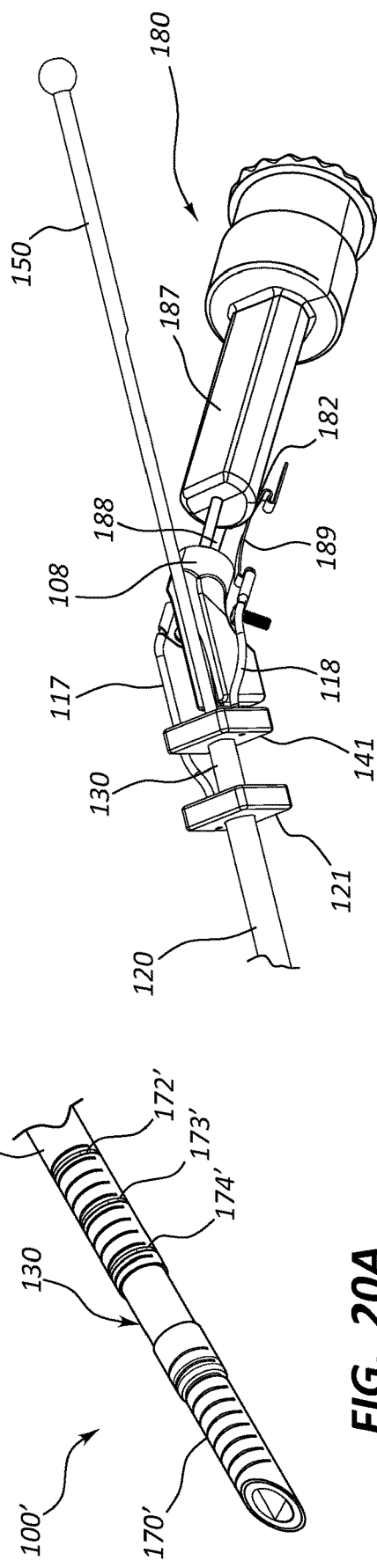

TUMOR ABLATION DEVICES AND RELATED METHODS

RELATED APPLICATIONS

This application claims priority to U.S. Provisional Application No. 62/426,825, filed on Nov. 28, 2016 and titled "Tumor Ablation Devices and Related Methods," and U.S. Provisional Application No. 62/426,816, filed on Nov. 28, 2016 and titled "Tumor Ablation Devices and Related Methods," both of which are hereby incorporated by reference in their entireties.

TECHNICAL FIELD

The present disclosure relates generally to the field of medical devices. More particularly, some embodiments relate to spinal tumor ablation devices and related systems and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 20 is a cross-sectional view of the medical device of FIG. 1 showing a thermal energy delivery probe that has been fully inserted into the port.

FIG. 20A is a perspective view of a distal portion of a medical device, according to another embodiment.

FIG. 21 is a perspective view of a portion of the medical device of FIG. 1 with various components removed to expose other components, wherein the perspective view shows an electrical connection between the thermal energy delivery probe and the tubular conductors.

DETAILED DESCRIPTION

Figure 1:
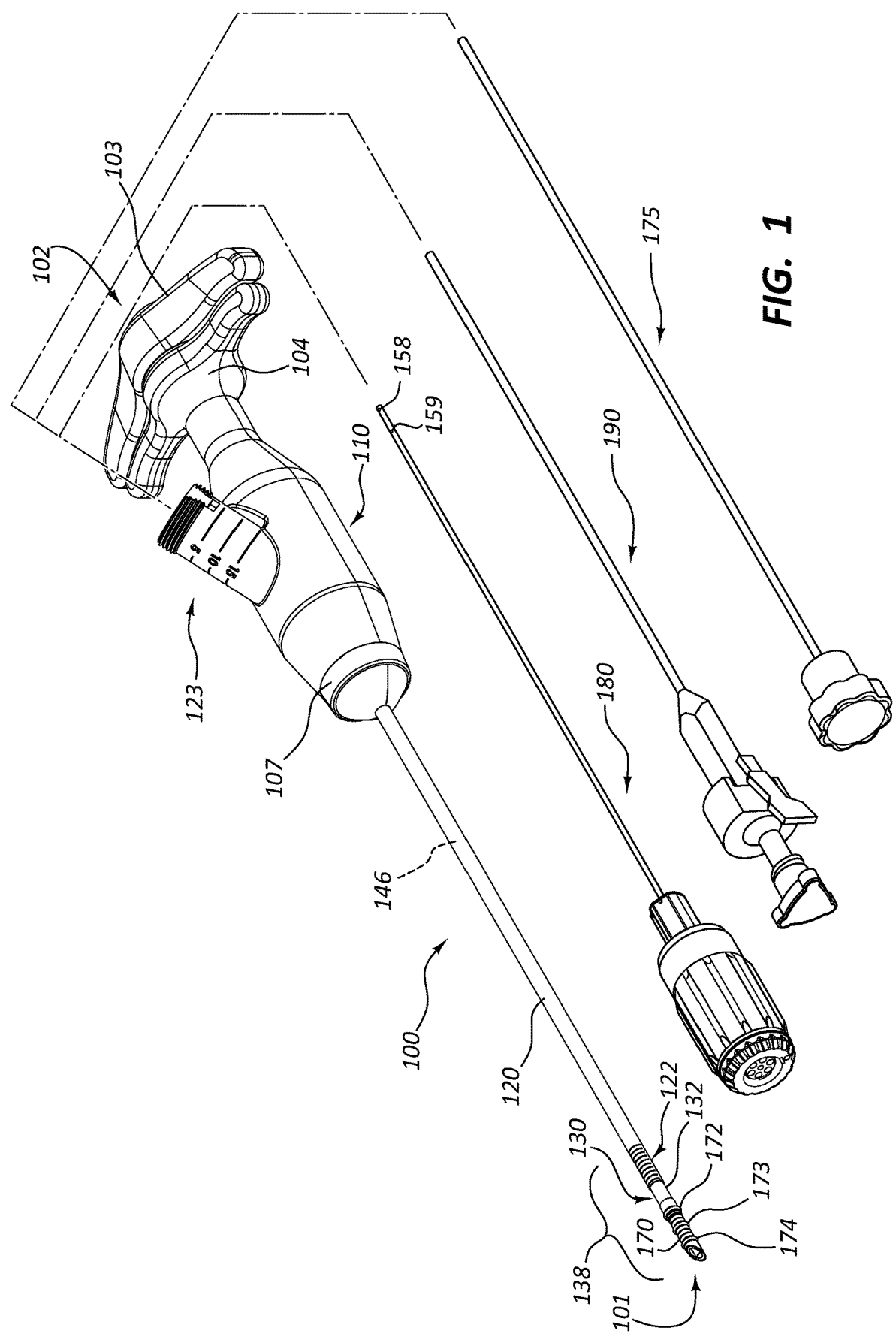
FIG. 1 is a perspective view of a medical device assembly comprising a medical device and three medical implements.

Spinal tumor ablation devices can be used to treat a tumor in a vertebra of a patient. For example, in some embodiments, a distal end of a spinal tumor ablation device may be inserted into a vertebra of a patient. In some instances, once the distal end of the spinal tumor ablation device is inserted into the vertebra of the patient, an articulating distal portion of the spinal tumor ablation device may be manipulated to position the tumor ablation device at a proper location within a tumor of the patient. The spinal tumor ablation device may then be activated. Activation of the spinal tumor ablation device may cause an electrical current (e.g., a radiofrequency current) to pass between a first electrode and a second electrode of the spinal tumor ablation device. As the electrical current passes between the first electrode and the second electrode, the current may pass through tissue of the patient, thereby heating (and potentially killing) the adjacent tissue (e.g., tumor cells). One or more temperature sensors may be used to measure the temperature of the heated tissue. Based on the information obtained from the one or more temperature sensors, the duration, position, and/or magnitude of the delivered thermal energy may be tailored to kill tissue within a desired region while avoiding the delivery of lethal amounts of thermal energy to healthy tissue. In some embodiments, once the tumor has been treated with thermal energy (e.g., radiofrequency energy), a cement may be delivered through a utility channel of the spinal tumor ablation device to stabilize the vertebra of the patient.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Two components may be coupled to each other even though they are not in direct contact with each other. For example, two components may be coupled to one another through an intermediate component. The phrases "attached to" or "attached directly to" refer to interaction between two or more entities which are in direct contact with each other and/or are separated from each other only by a fastener of any suitable variety (e.g., an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Figure 2:
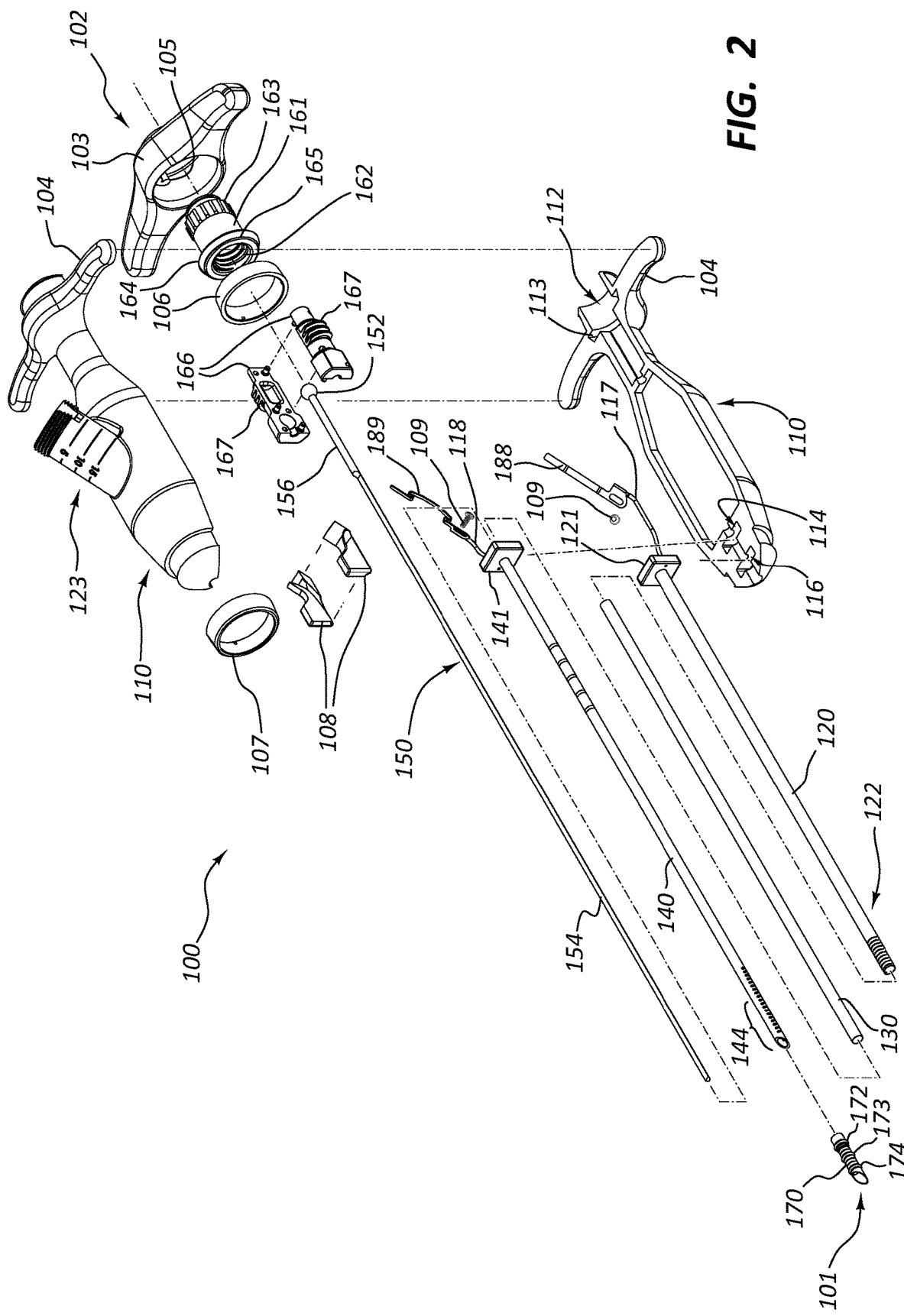
FIG. 2 is an exploded perspective view of the medical device of FIG. 1.
Figure 3:
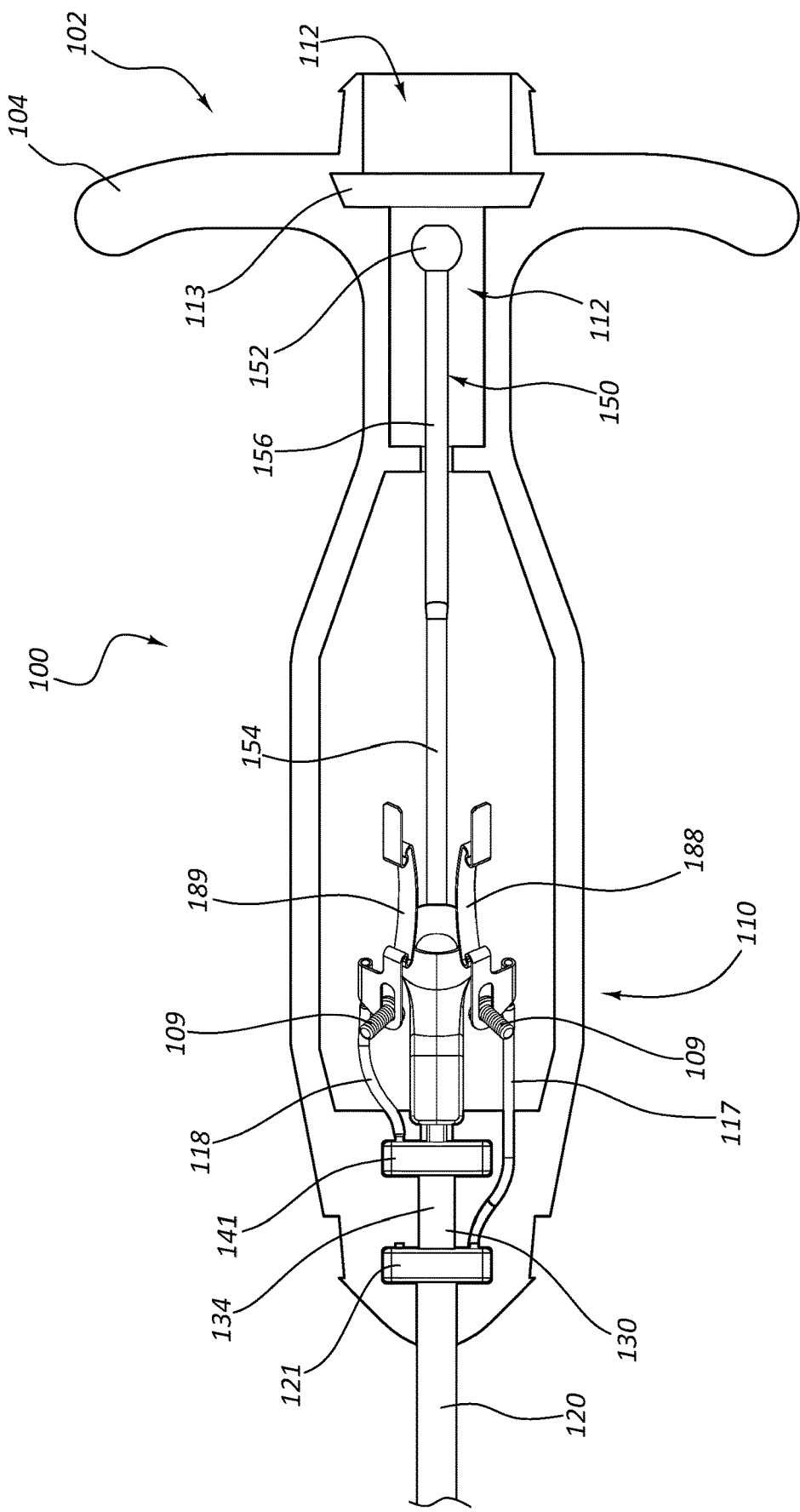
FIG. 3 is a side view of a portion of the medical device of FIG. 1 with a portion of the housing cut away to expose certain components.
Figure 4:
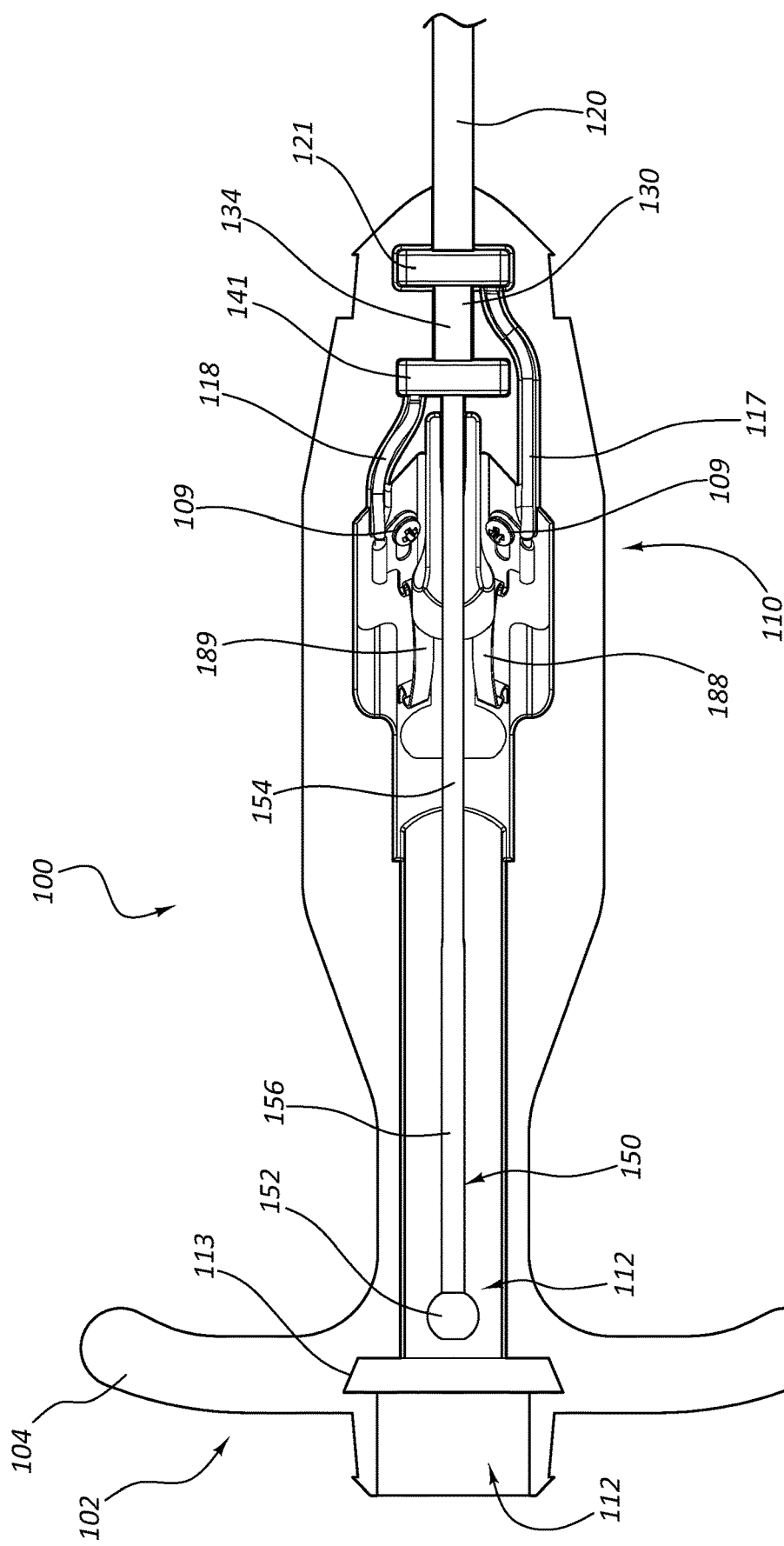
FIG. 4 is another side view of a portion of the medical device of FIG. 1 with a portion of the housing cut away to expose certain components.
Figure 5:
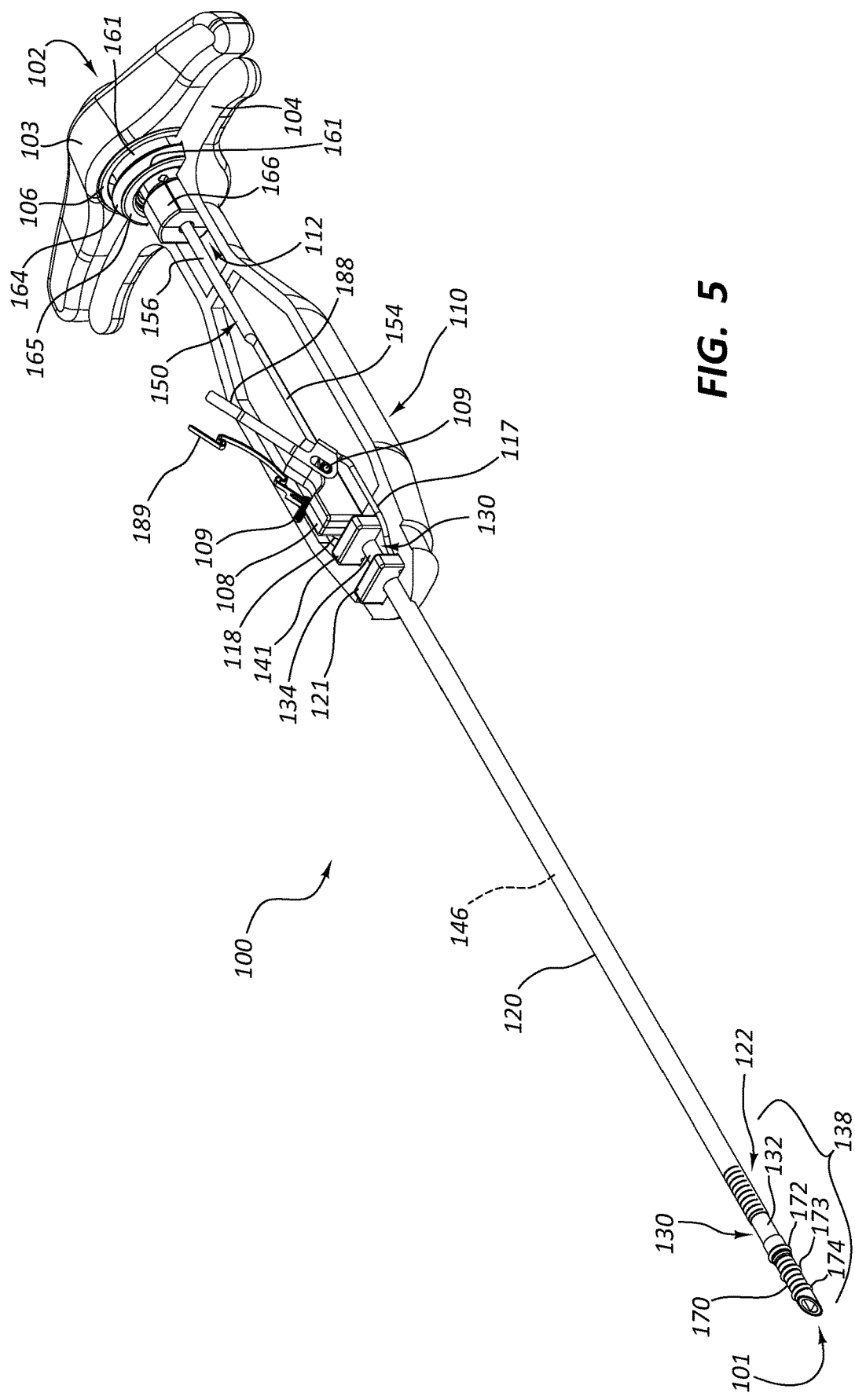
FIG. 5 is a perspective view of the medical device of FIG. 1, with a top half of the housing and an annular band removed to expose certain components.
Figure 6:
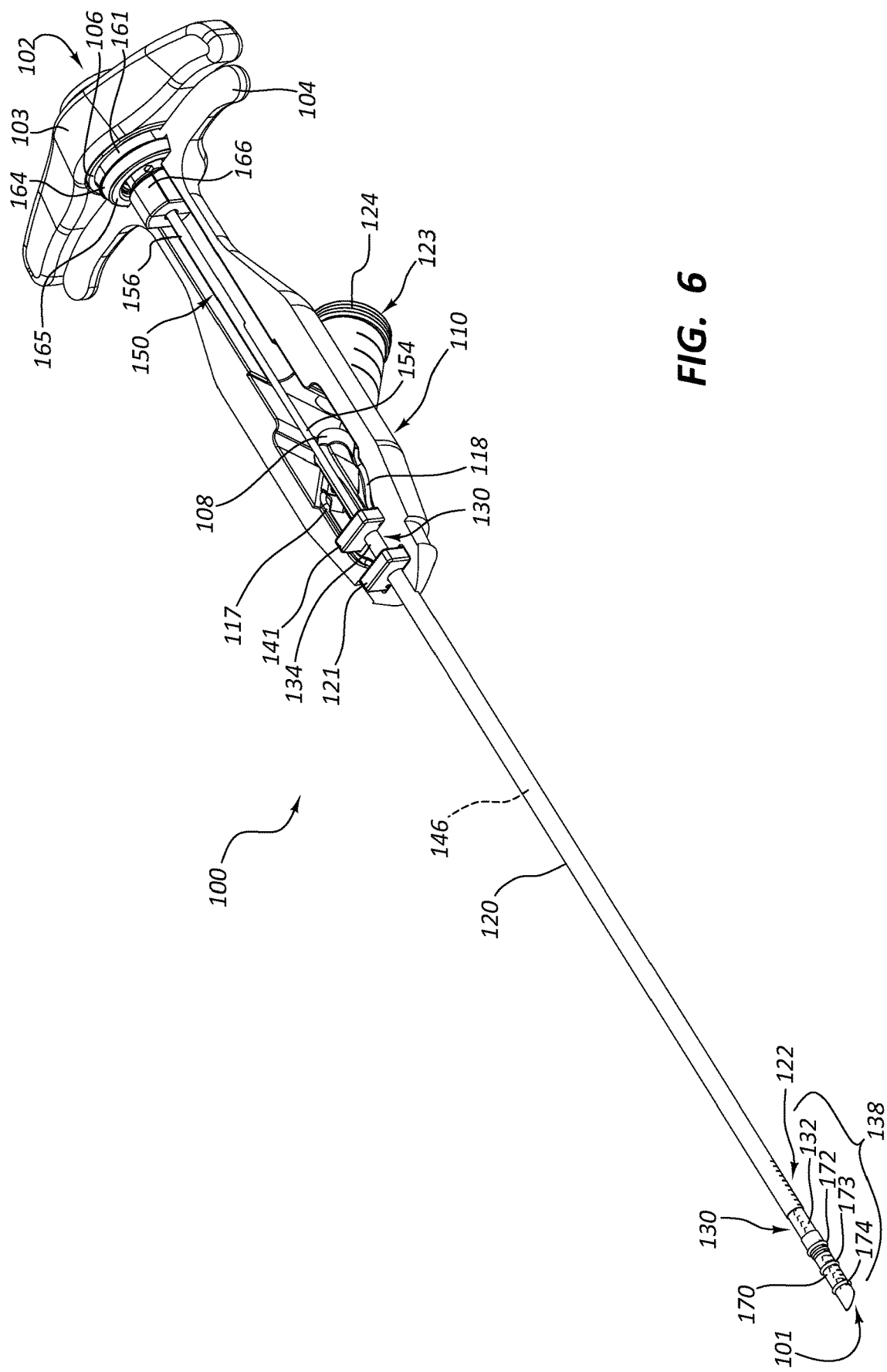
FIG. 6 is another perspective view of the medical device of FIG. 1, with the bottom half of the housing and an annular band removed to expose certain components.
Figure 7:
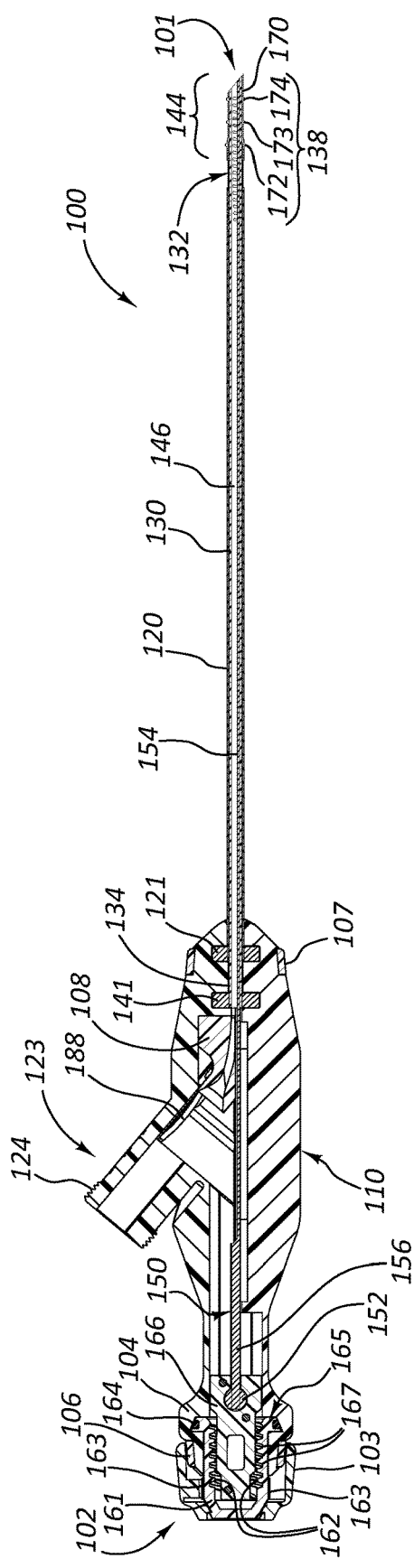
FIG. 7 is a cross-sectional view of the medical device of FIG. 1
Figure 8:
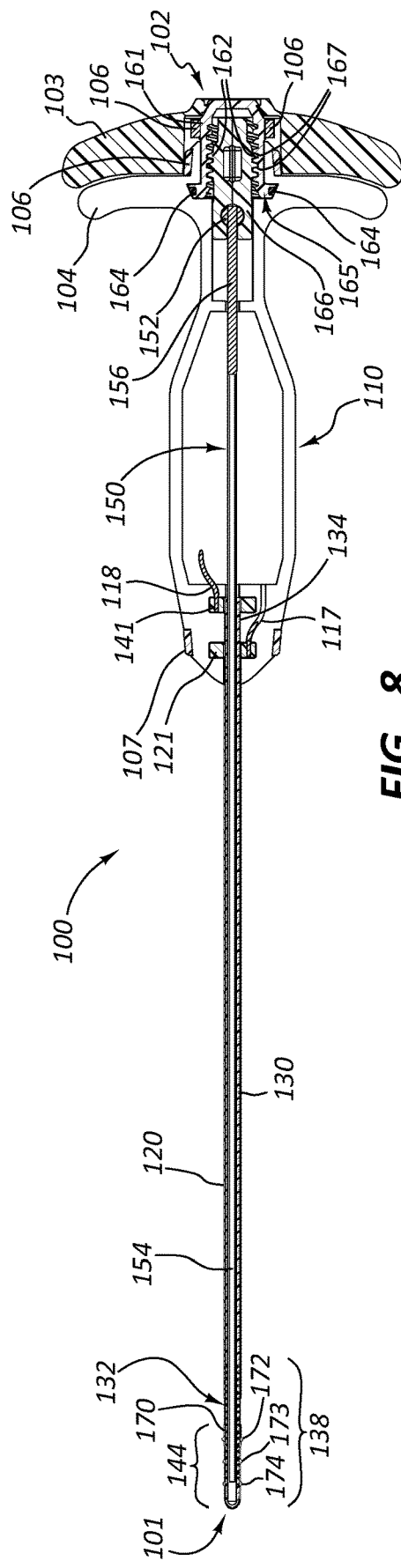
FIG. 8 is another cross-sectional view of the medical device of FIG. 1.
Figure 10:
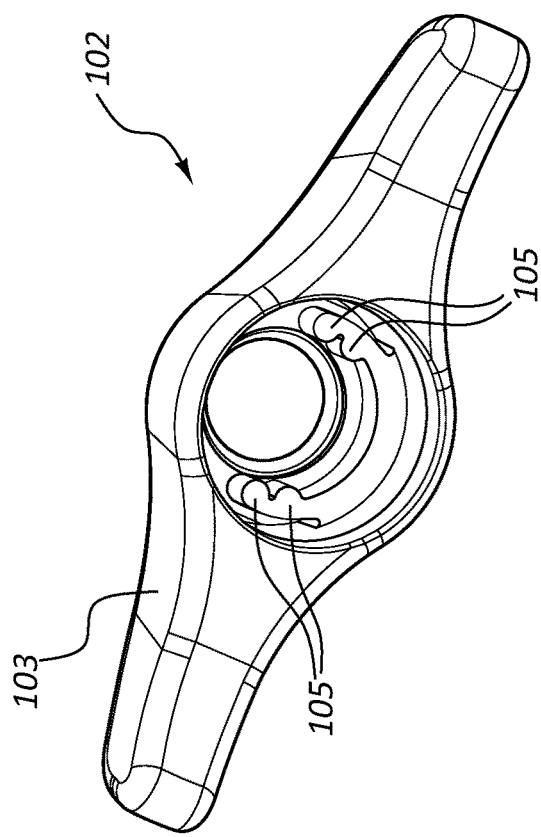
FIG. 10 is a perspective view of a portion of a handle of the medical device of FIG. 1.
Figure 9:
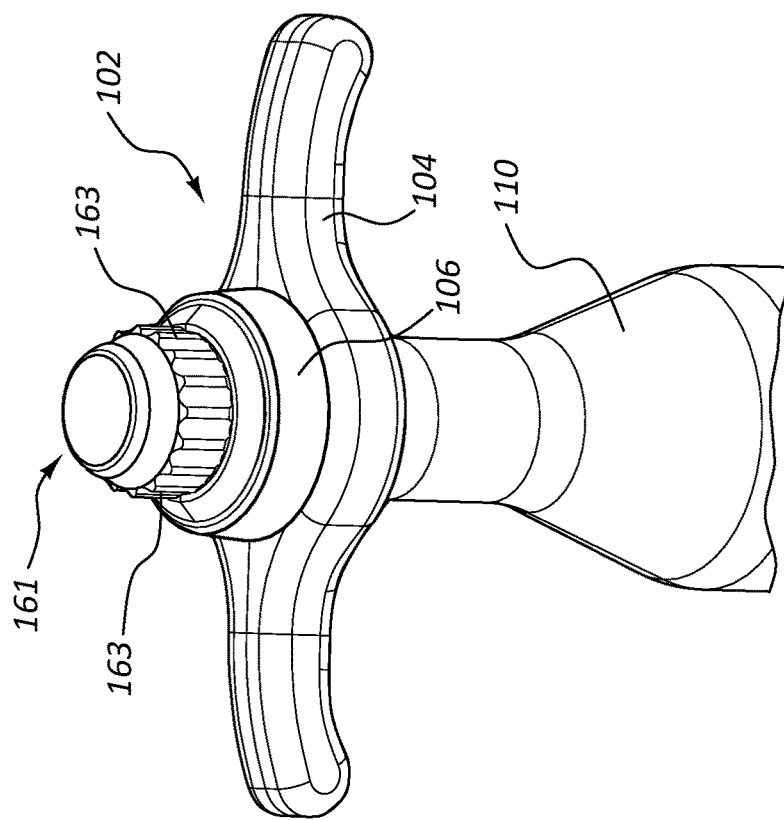
FIG. 9 is a perspective view of a portion of the medical device of FIG. 1.
Figure 11:
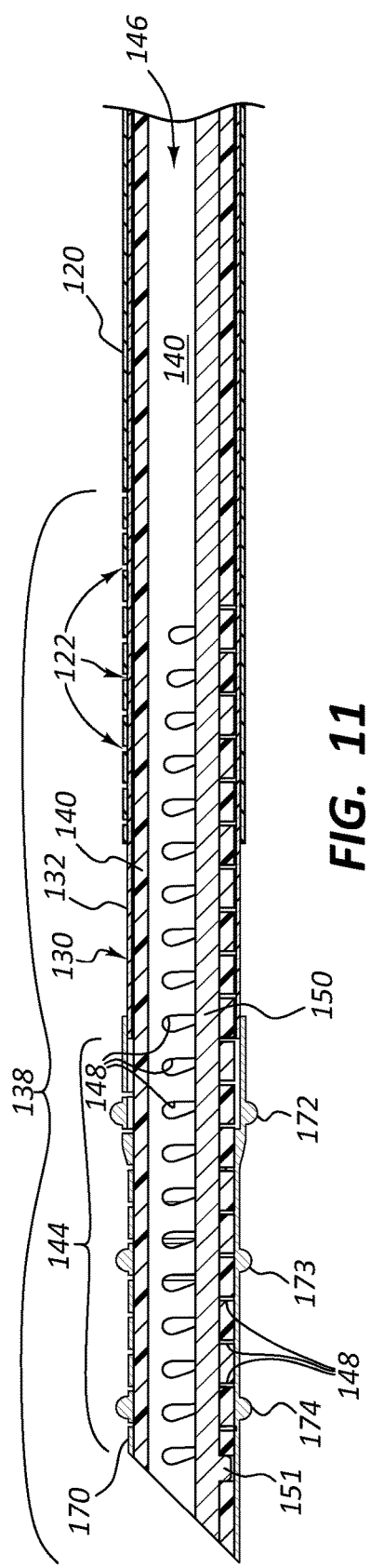
FIG. 11 is a cross-sectional view of a portion of the medical device of FIG. 1 showing an articulating distal portion in a linear configuration.
Figure 12:
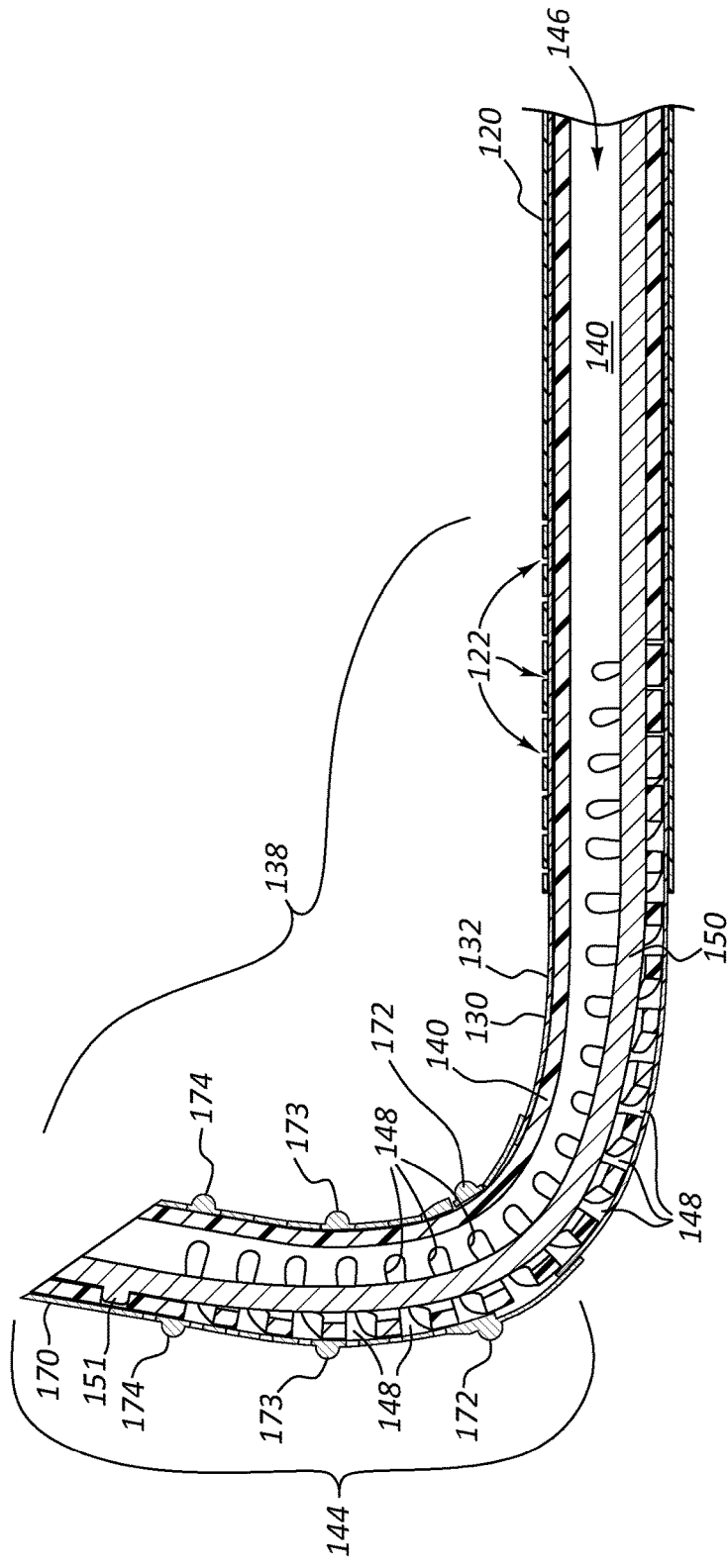
FIG. 12 is a cross-sectional view of a portion of the medical device of FIG. 1 showing an articulating distal portion in a first curved configuration.
Figure 13:
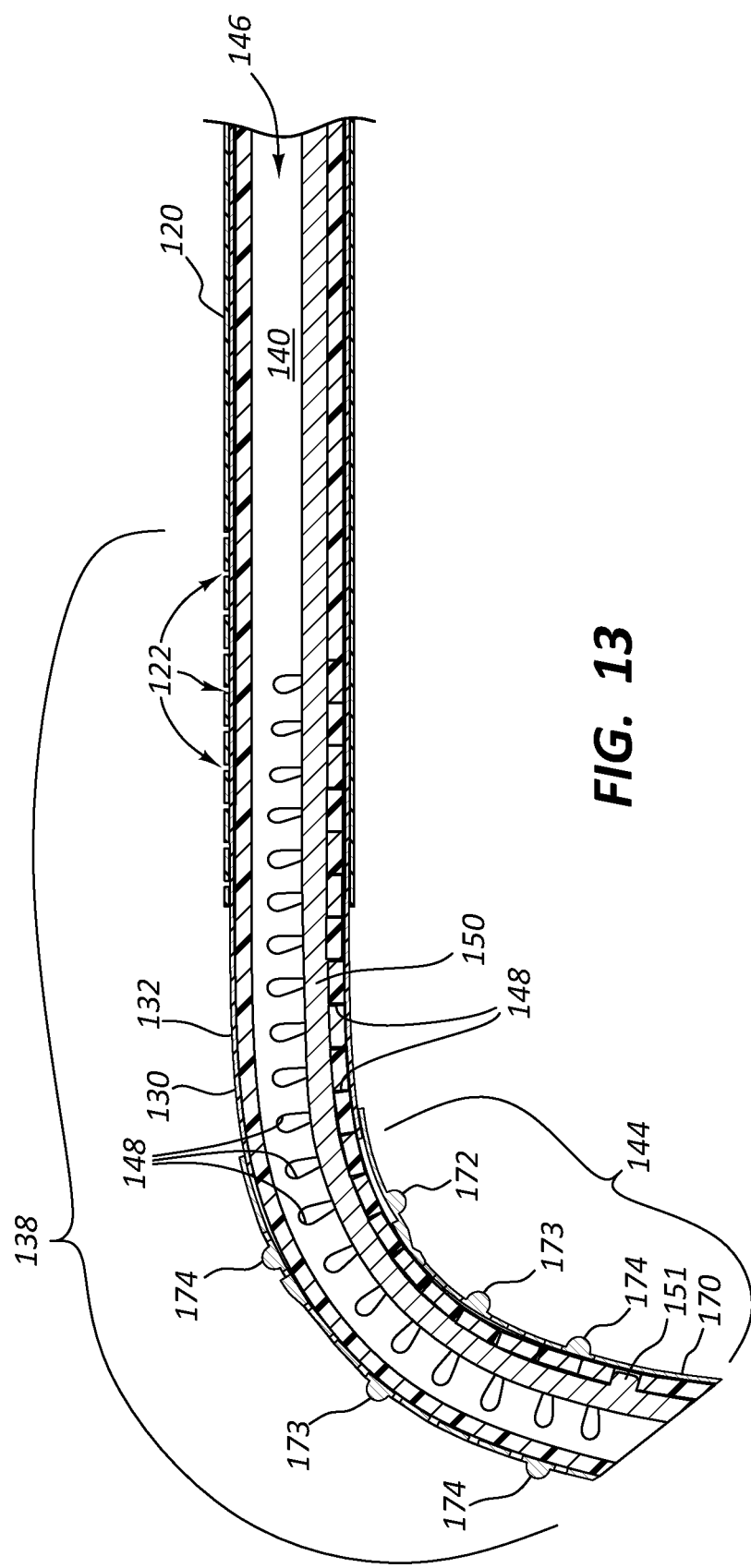
FIG. 13 is a cross-sectional view of a portion of the medical device of FIG. 1 showing an articulating distal portion in a second curved configuration.

FIGS. 1-13 provide various views of a medical device 100 (or portions thereof) or a medical device assembly for use in a spinal tumor ablation procedure. More particularly, FIG. 1 provides an assembled perspective view of a medical device assembly comprising a medical device 100 and related medical implements 175, 180, 190. FIG. 2 provides an exploded perspective view of the medical device 100. FIG. 3 is a side view of the medical device 100, with various components removed to expose other components. FIG. 4 is another side view of the medical device 100 with various component removed to expose other components. FIG. 5 is a perspective view of the medical device 100, with a first portion of the housing 110 and the annular band 107 removed to expose certain components. FIG. 6 is another perspective view of the medical device 100, with a second portion of the housing 110 and the annular band 107 removed to expose other components. FIGS. 7 and 8 provide alternative cross-sectional views of the medical device 100. FIGS. 9 and 10 provide perspective views showing different portions of a handle 102 of the medical device 100. FIG. 11 is a cross-sectional view of a distal portion of the medical device 100 in a linear configuration. FIGS. 12 and 13 are cross-sectional views of the distal portion of the medical device 100 in different non-linear configurations.

As shown in FIGS. 1-13, the medical device 100 includes, among other elements, a first tubular conductor 120, a tubular insulator 130, a second tubular conductor 140, a pointed distal end 101, an elongate shaft 150, a side port 123, an outer sleeve 170, a housing 110, and a handle 102.

The first tubular conductor 120 may be a metallic tube that extends from a proximal anchor 121 (e.g., a metallic anchor) to an open distal end. In some embodiments, the first tubular conductor 120 is rigid (or is rigid along most of its length). In some embodiments, the first tubular conductor 120 includes a plurality of slots 122 adjacent the open distal end of the first tubular conductor 120. The slots 122 may be perpendicular or angled relative to the primary axis of the first tubular conductor 120. In other embodiments, the first tubular conductor 120 lacks a plurality of slots.

The tubular insulator 130 may be at least partially disposed within the first tubular conductor 120. For example, the tubular insulator 130 may extend through the first tubular conductor 120. More particularly, in some embodiments, the tubular insulator 130 extends through the first tubular conductor 120 such that a proximal end of the tubular insulator 130 is proximal of the first tubular conductor 120 and a distal end of the tubular insulator 130 is distal of the first tubular conductor 120. The tubular insulator 130 may be made from any suitable insulating material, such as polymeric insulating materials. Examples of suitable polymeric insulating materials include polyimide, polyetheretherketone (PEEK), and polyether block amides (e.g., PEBAX®).

The second tubular conductor 140 may be a metallic tube that extends from a proximal anchor 141 (e.g., a metallic anchor) to an open distal end. In some embodiments, the second tubular conductor 140 is rigid (or is rigid along most of its length). The second tubular conductor 140 may be at least partially disposed within the tubular insulator 130. For example, the second tubular conductor 140 may extend through the tubular insulator 130 such that a distal portion 144 of the second tubular conductor 140 is disposed distal of the tubular insulator 130. The second tubular conductor 140 may form a utility channel 146 that extends from a proximal opening of the second tubular conductor 140 to a distal opening at the distal end of the second tubular conductor 140. In some embodiments, the portion 144 of the second tubular conductor 140 that is disposed distal of the tubular insulator 130 is longitudinally offset from the first tubular conductor 120 by an exposed portion 132 of the tubular insulator 130. The exposed portion 132 of the tubular insulator 130 may have a length of between 0.3 cm and 1.0 cm. Stated differently, the gap between the distal portion 144 of the second tubular conductor 140 and the distal end of the first tubular conductor 120 may be between 0.3 cm and 1.0 cm.

In some embodiments, the second tubular conductor 140 includes a plurality of slots 148 adjacent the distal end of the second tubular conductor 140. The slots 148 may be perpendicular or angled relative to the primary axis of the second tubular conductor 140. The plurality of slots 148 may be disposed opposite the slots 122 of the first tubular conductor 120.

In some embodiments, the anchor 121 at the proximal end of the first tubular conductor 120 may be electrically coupled to an electrical contact 188 via a wire 117. Similarly, in some embodiments, the anchor 141 at the proximal end of the second tubular conductor 140 may be electrically coupled to another electrical contact 189 via another wire 118. In some embodiments, the wires 117, 118 may travel through channels in the housing 110. In some embodiments, one or both of the electrical contacts 188, 189 are leaf spring contacts. When the electrical contacts 188, 189 are coupled to a power source, the first tubular conductor 120 and the second tubular conductor 140 may function as electrodes with opposite polarity. In some embodiments, the electrical contacts 188, 189 are secured to the housing 110 via one or more screws 109.

The elongate shaft 150 may be at least partially disposed within the utility channel 146 of the second tubular conductor 140. In some embodiments, the elongate shaft 150 is coupled to the second tubular conductor 140 such that manipulation of the elongate shaft 150 causes articulation of an articulating distal portion 138 of the medical device 100. For example, in some embodiments, only a distal portion 151 of the elongate shaft 150 is attached (e.g., welded) to the second tubular conductor 140 (see FIGS. 11-13) while the remaining portion of the elongate shaft 150 is unattached from the second tubular conductor 140. In other words, the distal portion 151 of the elongate shaft 150 may be attached to the second tubular conductor 140 adjacent a distal end of the second tubular conductor 140. By displacing the elongate shaft 150 relative to the proximal end of the second tubular conductor 140 as described in greater detail below in connection with reference to FIGS. 11-13, the articulating distal portion 138 of the medical device 100 may be displaced (e.g., transition from a linear configuration to a non-linear configuration and vice versa).

In the depicted embodiment, the elongate shaft 150 includes a bulbous proximal end 152. Stated differently, the elongate shaft 150 may include a ball at its proximal end. A distal portion 154 of the elongate shaft 150 may have a semicircular (e.g., D-shaped) cross-section. Due, in part, to the semicircular cross section of the elongate shaft 150, the elongate shaft 150 may flex when a force is applied to the elongate shaft 150 and then return to a linear position when the force is removed. The distal portion 154 of the elongate shaft 150 may extend from the distal end of the elongate shaft 150 to a position that is proximal of the proximal opening of the second tubular conductor 140. In some embodiments, the bulbous proximal end 152 of the elongate shaft 150 and the distal portion 154 of the elongate shaft 150 are separated by an intermediate portion 156 of the elongate shaft 150 that has a circular cross-section.

Due to the semicircular shape of the distal portion 154 of the elongate shaft 150, the elongate shaft 150 may occupy only a portion of the space within the utility channel 146 of the second tubular conductor 140. The remaining portion (e.g., a D-shaped portion) of the utility channel 146 may be used for other purposes, such as for obtaining a biopsy sample, positioning temperature sensors, and/or delivering cement to a vertebra of a patient as described in greater detail below.

The port 123 may be configured to provide access to a proximal opening of the utility channel 146. Stated differently, the port 123 may be in fluid communication with the utility channel 146 of the second tubular conductor 140. In the depicted embodiment, the port 123 is a side port that is disposed proximal of the second tubular conductor 140. The port 123 may be designed to accommodate various medical implements, such as one or more of a thermal energy delivery probe 180 having one or more temperature sensors 158, 159, an elongate cutting instrument 175, and a cement delivery cartridge 190 (see FIG. 1). Stated differently, in some embodiments, the medical device 100 is configured to permit sequential (1) insertion of an elongate cutting instrument 175 into the port 123, (2) removal of the elongate cutting instrument 175 from the port 123, (3) insertion of a thermal energy delivery probe 180 into the port 123, (4) removal of the thermal energy delivery probe 180 from the port 123, and (5) insertion of the cement delivery cartridge 190 across the port 123. In some embodiments, the port 123 includes indicia that help the practitioner to determine the position of one or more temperature sensors as described in greater detail below.

The outer sleeve 170 may be attached (e.g., laser welded) to the distal portion 144 of the second tubular conductor 140 (see FIG. 11). In the depicted embodiment, the outer sleeve 170 is offset from the first tubular conductor 120. In other words, the outer sleeve 170 is not attached to the first tubular conductor 120. In some embodiments, the outer sleeve 170 generally has an outer diameter that is substantially identical to the outer diameter of the first tubular conductor 120. In some embodiments, the outer sleeve 170 includes one or more protrusions 172, 173, 174 (e.g., radiopaque protrusions) or intrusions (not shown). The one or more protrusions 172, 173, 174 or intrusions may facilitate fluoroscopic visualization as described in greater detail below. In some embodiments, the outer sleeve 170 is a metallic tube.

In some embodiments, the medical device 100 has a pointed distal end 101. The pointed distal end 101 may be formed from one or both of the second tubular conductor 140 and the outer sleeve 170. The pointed distal end 101 may be configured to facilitate penetration of bone within the vertebra of a patient.

The housing 110 may be configured to encompass and/or protect various components of the medical device 100. For example, in the depicted embodiment, the housing 110 encompasses, at least in part, a rotatable sleeve 161, a casing 166, an O-ring 164, and a guide insert 108. In some embodiments, the rotatable sleeve 161 has the general shape of a top hat. Indeed, in the depicted embodiment, the rotatable sleeve 161 includes an annular brim 165 that extends radially outward from the base of the rotatable sleeve 161. Stated differently, the rotatable sleeve 161 may comprise a brim 165 that extends radially outward. The O-ring 164 may be positioned around the brim 165 of the rotatable sleeve 161. The rotatable sleeve 161 may include interior threads 162 that are configured to mate with exterior threads 167 on the casing 166. The casing 166 may be designed to encompass a proximal end of an elongate shaft 150. For example, in some embodiments, the casing 166 encompasses the bulbous proximal end 152 of the elongate shaft 150. In some embodiments, the casing 166 is formed by attaching a first half of the casing 166 that includes a hemisphere-shaped indentation with a second half of the casing 166 that includes another hemisphere-shaped indentation. The indentations on each half of the casing 166 may cooperate to form a spherical pocket that accommodates a bulbous proximal end 152 of the elongate shaft 150.

The guide insert 108 may be disposed within the housing 110 to facilitate insertion of one or more elongate instruments into the utility channel 146 of the second tubular conductor 140. For example, in some embodiments, the guide insert 108 is formed from a first half and a second half that together combine to form a funnel-shaped surface that directs elongate instruments into the utility channel 146.

The housing 110 may include various recesses (see, e.g., FIG. 2). For example, the housing 110 may include a first recess 112 that is configured to accommodate both the rotatable sleeve 161 and the casing 166 that is partially disposed within the rotatable sleeve 161. The first recess 112 may jut out to form a disk-shaped cavity 113 that is designed to snugly accommodate the annular brim 165 of the rotatable sleeve 161. The housing 110 may also include a second recess 114 that is designed to accommodate (e.g., secure) an anchor 141 at the proximal end of the second tubular conductor 140. The housing 110 may also include a third recess 116 that is configured to accommodate (e.g., secure) an anchor 121 at the proximal end of the first tubular conductor 120. In the depicted embodiment, the first recess 112 is disposed proximal of the second recess 114, and the second recess 114 is disposed proximal of the third recess 116. Due to the relative position of the second recess 114 relative to the third recess 116, the anchors 121, 141 (and therefore the proximal ends of the tubular conductors 120, 140) are longitudinally offset from one another. Stated differently, the anchor 121 at the proximal end of the first tubular conductor 120 may be disposed distal of the anchor 141 at the proximal end of the second tubular conductor 140. In this manner, at least a portion of the second tubular conductor 140 is fixedly disposed relative to the first tubular conductor 120. A portion 134 of the tubular insulator 130 may be disposed around the second tubular conductor 140 within the gap between the anchor 121 for the first tubular conductor 120 and the anchor 141 for the second tubular conductor 140. In some embodiments, the gap is greater than 0.5 cm. For example, in some embodiments, the gap is between 0.5 and 2.0 cm in length.

In some embodiments, the first portion of the housing 110 and the second portion of the housing 110 are held together by one or more of an adhesive, a fastener, and annular bands 106, 107.

The handle 102 may include a first portion 103 (e.g., a proximal portion) and a second portion 104 (e.g., a distal portion). The first portion 103 of the handle 102 may include one or more flexible arms and one or more teeth 105 that project radially inward from the one or more flexible arms. The one or more teeth 105 may be configured to engage with one or more outer protrusions 163 on the rotatable sleeve 161. The first portion 103 of the handle 102 may be rotatable relative to the second portion 104 of the handle 102. As described in further detail below, rotation of the first portion 103 of the handle 102 may cause displacement (e.g., articulation) of a distal portion 138 of the medical device 100. Stated differently, manipulation of the handle 102 may cause displacement of the articulating distal portion 138. In some embodiments, the second portion 104 of the handle 102 is integrally formed with the housing 110.

The medical device 100 may be used in one or more medical procedures, such as procedures to treat a spinal tumor in one or more vertebral bodies of a patient. For example, some embodiments of a medical procedure may involve obtaining the medical device 100 and inserting a distal end 101 of the medical device 100 into a vertebral body of a patient (e.g., a sedated patient in the prone position). In embodiments in which the distal end 101 of the medical device 100 is pointed, the pointed distal end 101 may facilitate penetration of bone within the vertebra of the patient. In some embodiments, the medical device 100 has sufficient strength to prevent buckling of the medical device 100 as the distal end of the medical device 100 is inserted within a vertebra (e.g., across the cortical bone) of the patient. In some embodiments, the distal end 101 of the medical device 100 is inserted into the patient via an introducer (not shown). In other embodiments, the distal end 101 of the medical device 100 is inserted into the patient without using an introducer.

Figure 15:
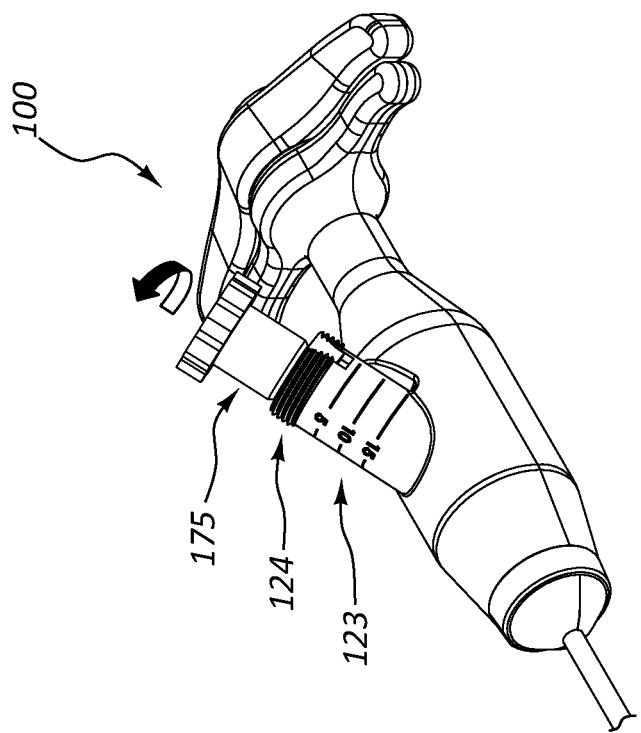
FIG. 15 is a perspective view of a portion of the medical device of FIG. 1, wherein the perspective view shows rotation of the elongate cutting instrument relative to the port.
Figure 14:
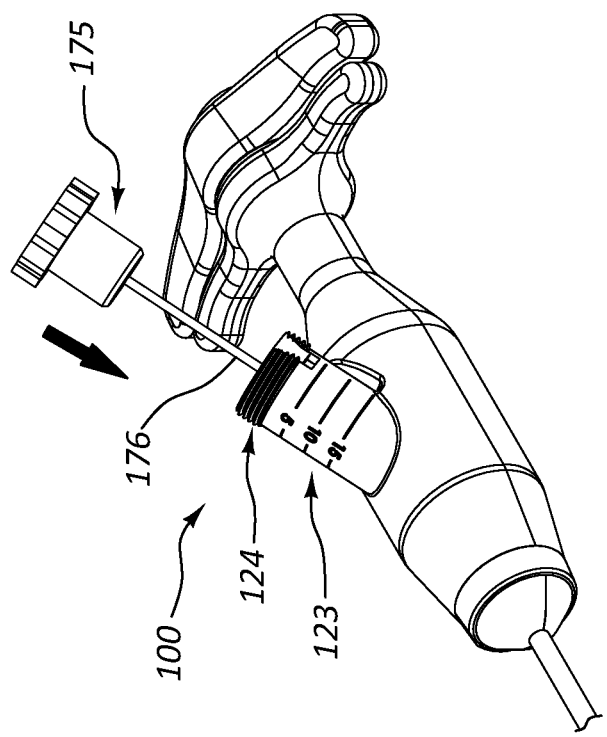
FIG. 14 is a perspective view of a portion of the medical device of FIG. 1, wherein the perspective view shows insertion of an elongate cutting instrument into a port.

In some circumstances, and with particular reference to FIGS. 14-17, once the distal end 101 of the medical device 100 is disposed within a vertebra of the patient, an elongate cutting instrument 175 may be inserted through the port 123 of the medical device 100 and into the utility channel 146 of the second tubular conductor 140. The guide insert 108 may provide a funnel shaped opening that guides the elongate cutting instrument 175 into the utility channel 146. The elongate cutting instrument 175 may include an elongate shaft 176 that terminates in a serrated end 177 (see FIG. 17). The elongate shaft 176 may be flexible, thereby allowing the elongate shaft 176 to adopt a non-linear configuration. As the elongate cutting instrument 175 is inserted through the port 123, the serrated end 177 of the elongate shaft 176 may emerge from an opening at the distal end 101 of the utility channel 146 and enter into tissue of the patient. By rotating the elongate cutting instrument 175 as shown in FIG. 15, the serrated end 177 of the elongate cutting instrument 175 may cut into tissue of the patient to obtain a biopsy sample. Once the biopsy sample has been cut from the patient, the elongate cutting instrument 175 may be removed from the patient, and the sample may subjected to one or more tests.

Figure 16:
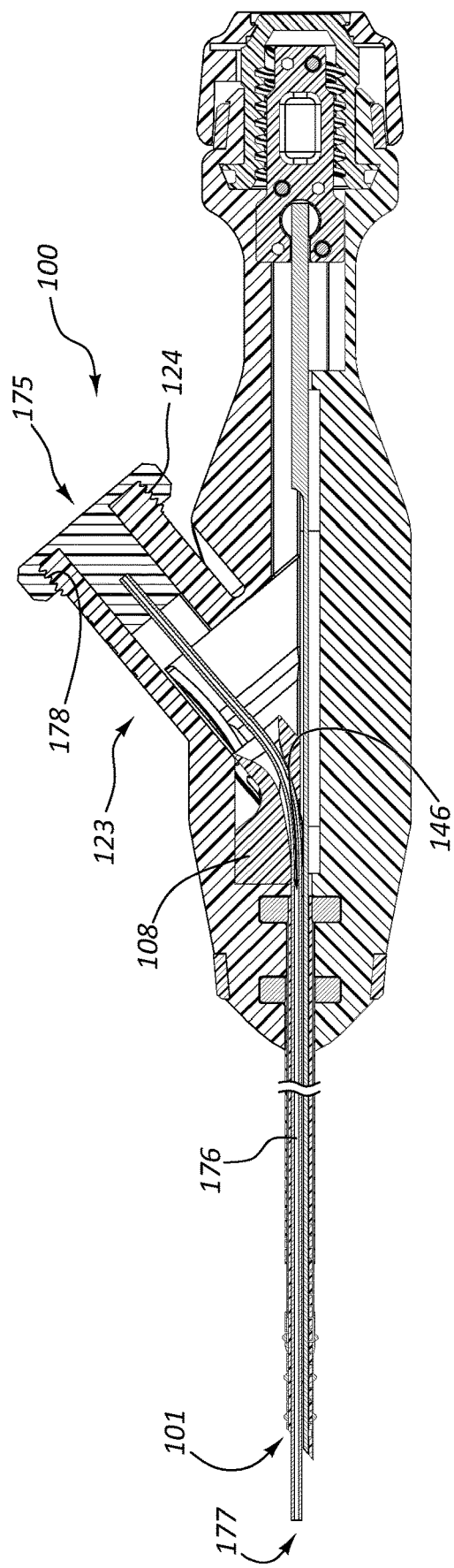
FIG. 16 is a cross-sectional view of the medical device of FIG. 1 with the elongate cutting instrument in a fully inserted configuration.
Figure 17:
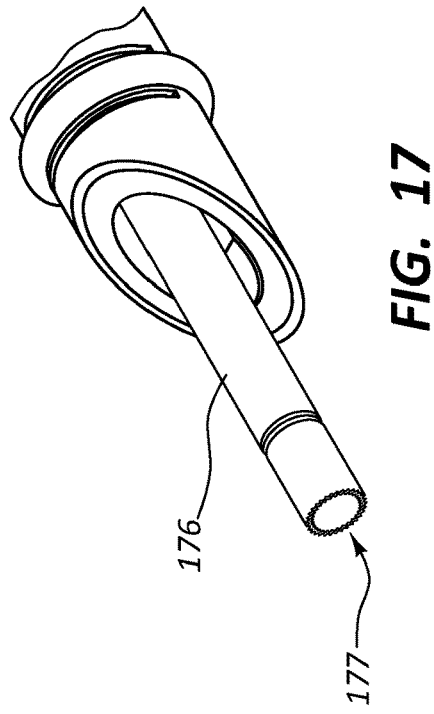
FIG. 17 is a perspective view of a portion of the medical device of FIG. 1 that shows a distal end of the medical device when the elongate cutting instrument is in the fully inserted configuration.
Figure 19:
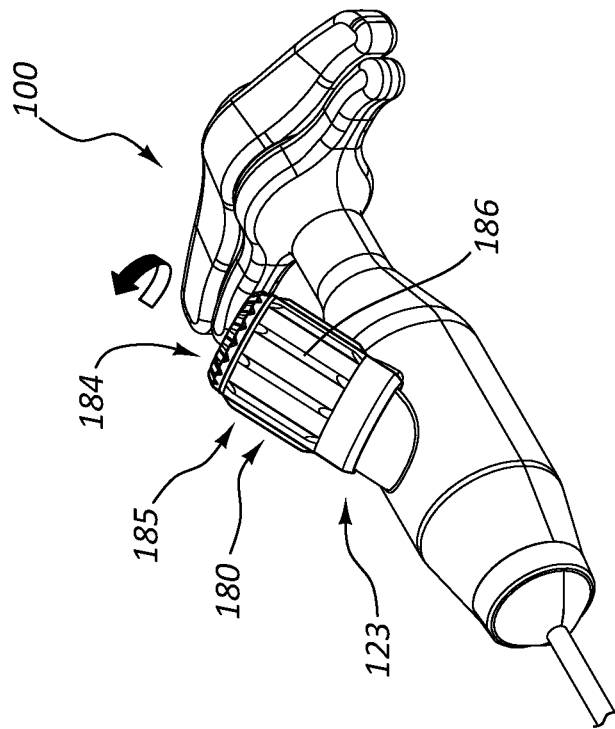
FIG. 19 is a perspective view of a portion of the medical device of FIG. 1, wherein the perspective view shows rotation of the thermal energy delivery probe relative to the port.
Figure 18:
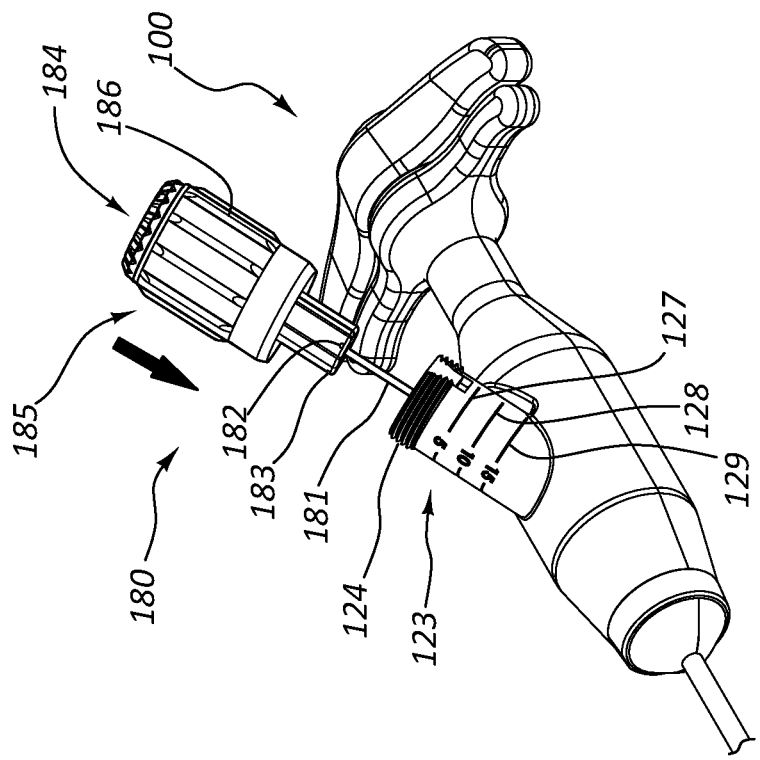
FIG. 18 is a perspective view of a portion of the medical device of FIG. 1, wherein the perspective view shows insertion of a thermal energy delivery probe into a port.

In some embodiments, the elongate cutting instrument 175 includes interior threads 178 that mate with exterior threads 118 on the port 123 (see FIG. 16). Mating of the interior threads 178 of the elongate cutting instrument 175 with exterior threads 124 on the port 123 may help a practitioner determine or estimate the position of the serrated end 177 of the elongate cutting instrument 175.

In some embodiments, once the distal end 101 of the medical device 100 is disposed within a vertebra of the patient, the articulating distal portion 138 of the medical device 100 may be displaced. For example, the articulating distal portion 138 of the medical device 100 may be transitioned from a linear configuration (FIG. 11) to one or more of a non-linear configuration (FIGS. 12 and 13). To effectuate this transition, the proximal portion 103 of the handle 102 may be rotated relative to the housing 110. As the proximal portion 103 of the handle 102 is rotated, the inward-extending teeth 105 may engage with protrusions 163 on the rotatable sleeve 161, thereby causing the rotatable sleeve 161 to rotate.

As the rotatable sleeve 161 is rotated, the casing 166 is proximally or distally displaced relative to the housing 110. More specifically, due to the interaction of the interior threads 162 of the rotatable sleeve 161 with the exterior threads 167 of the casing 166, the casing 166 is displaced in a proximal direction when the rotatable sleeve 161 is rotated in a first direction and in a distal direction when the rotatable sleeve 161 is rotated in a second direction that is opposite to the first direction. In the depicted embodiment, when the rotatable sleeve 161 is rotated, the rotatable sleeve 161 is not appreciably displaced in a proximal direction or a distal direction due to the interactions of the O-ring 164 and/or the brim 165 of the rotatable sleeve 161 with the cavity 113 of the first recess 112. In other words, in some embodiments, the rotatable sleeve 161 does not move in a proximal direction or a distal direction with respect to the housing 110 because the rotatable sleeve 161 is snugly positioned within the disk-shaped cavity 113 of the first recess 112. In the depicted embodiment, the casing 166 does not rotate due to the interaction of one or more flat surfaces of the casing 166 with the first recess 112.

As the casing 166 is displaced in a proximal direction or a distal direction, the casing 166 may exert a force on the elongate shaft 150, thereby causing the elongate shaft 150 to be displaced in a proximal direction or in a distal direction relative to the housing 110, the anchors 121, 141, and/or at least a portion of the second tubular body 140. Stated differently, due to the engagement of the casing 166 with the bulbous proximal end 152 of the elongate shaft 150, the casing 166 may exert a proximal or distal force on the elongate shaft 150, causing the elongate shaft 150 to be displaced in a proximal direction or a distal direction.

As the elongate shaft 150 is displaced in a distal direction, the distal portion 138 of the medical device 100 may transition from the linear configuration (FIG. 11) to a non-linear configuration (FIG. 12) in which the slots 148 of the second tubular conductor 140 are disposed on the convex side of the bend, and the slots 122 of the first tubular conductor 120 are disposed on the concave side of the bend. In contrast, when the elongate shaft 150 is displaced in a proximal direction, the distal portion 138 of the medical device 100 may transition to a non-linear configuration in which the slots 148 of the second tubular conductor 140 are disposed on the concave side of the bend while the slots 122 of the first tubular conductor 120 are disposed on the convex side of the bend (see FIG. 13). As the elongate shaft 150 is displaced in proximal and distal directions, the distal portion 138 of the medical device 100 may transition from a linear configuration to a non-linear configuration in only a single plane. Stated differently, in some embodiments, movement of the distal portion 138 of the medical device 100 is limited to a single plane. By rotating the rotatable sleeve 161 a selected amount, the articulating distal portion 138 may be bent to a selected degree.

In some instances, articulation of the distal portion 138 of the medical device 100 may facilitate placement of the distal portion 138 of the medical device 100 at a desired location for ablation. Stated differently, the medical device 100 may have an active steering capability that enables navigation to and within a tumor. In some instances, articulation of the distal portion 138 of the medical device 100 may additionally or alternatively mechanically displace tissue (e.g., tumor cells) within the vertebra of the patient. For example, the medical device 100 may function as an articulating osteotome that enables site-specific cavity creation. Stated differently, the articulating distal portion 138 of the medical device 100 may be robust enough to facilitate navigation through hard tissue of a patient. Thus, in the manner described above, manipulation of the handle 102 may cause displacement of both the elongate shaft 150 and the articulating distal portion 138 of the medical device 100. Stated differently, the practitioner may articulate a distal portion 138 of the medical device 100 such that the distal portion 138 transitions from a linear configuration to a non-linear configuration (and vice versa).

In some embodiments, the medical device 100 is configured to prevent a practitioner from exerting an excessive amount of torque on the rotatable sleeve 161, which could potentially damage one or more components (e.g., the elongate shaft 150 or the articulating distal portion 138) of the medical device 100. For example, in some embodiments, the one or more teeth 105 that project radially inward from arms of the proximal portion 103 of the handle 102 (see FIG. 10) may be configured to deflect outward when too much torque is provided, thereby causing the proximal portion 103 of the handle 102 to disengage from the protrusions 163 on the rotatable sleeve 161 (see FIG. 9). More particularly, at a selected torque—for example a torque ranging from greater than about 0.5 inch-pounds but less than about 7.5 inch-pounds—the proximal portion 103 of the handle 102 may disengage from the protrusions 163 on the rotatable sleeve 161. Such disengagement prevents the practitioner from exerting an excessive amount of force on the rotatable sleeve 161. Stated differently, the proximal portion 103 of the handle 102 may function as a torque limiter.

Once the distal tip 101 of the medical device 100 has been inserted into the patient and the articulating distal portion 138 of the medical device has been positioned at the desired location (e.g., within a tumor) in a preferred orientation (e.g., such that the distal portion 138 is bent), the medical device 100 may be activated for ablation within a vertebra of a patient such that an electrical current flows between the distal portion 144 of the second tubular conductor 140 to the first tubular conductor 120 via tissue within the vertebra of the patient. Stated differently, the first tubular conductor 120 may function as first electrode and the second tubular conductor 140 may function as a second electrode such that an electrical current flows between the first electrode and the second electrode via tissue within a vertebral body of the patient. In some embodiments, the temperature of tissue within the vertebral body of the patient may be measured as the electrical current flows between the first electrode and the second electrode. In some embodiments, the process of treating a spinal tumor does not involve advancement or retraction of the electrodes relative to one another. In some embodiments, the process of treating a spinal tumor does not involve displacement of the first electrode and/or the second electrode via a spring. Stated differently, in some embodiments, neither the first electrode nor the second electrode is coupled to a spring.

To activate the medical device 100 for ablation, the practitioner may, as shown in FIGS. 18-21, insert a thermal energy delivery probe 180 through the port 123 such that the thermal energy delivery probe 180 is at least partially disposed within the utility channel 146 of the second tubular conductor 140. The guide insert 108 may facilitate such insertion by guiding the thermal energy delivery probe 180 into the utility channel 146. In the depicted embodiment, the thermal energy delivery probe 180 includes a shell 186, a main body 187, a stylet 181, a first electrical contact 182, a second electrical contact 183, and an adaptor 184 for connecting to a power supply. In some embodiments, the shell 186 of the thermal energy delivery probe 180 is rotatable relative to a main body 187 of the thermal energy delivery probe 180. In some embodiments, the shell 186 of the thermal energy delivery probe 180 may be rotated (see FIG. 19) relative to the port 123 to selectively couple the thermal energy delivery probe 180 to the port 123. In some embodiments, the thermal energy delivery probe 180 may further include interior threads 157 that are configured to engage with exterior threads 124 on the port 123. In other words, rotation of the thermal energy delivery probe 180 relative to the port 123 may cause thread-based displacement of the thermal energy delivery probe 180 relative to the second tubular conductor 140. Stated differently, rotating the thermal energy delivery probe 180 relative to a side port 123 of the medical device 100 may result in adjustment of the position(s) of one or more temperature sensors 158, 159 that are attached to the stylet 181 of the thermal energy delivery probe 180.

Upon insertion, the first electrical contact 182 of the thermal energy delivery probe 180 may be in electrical communication with the electrical contact 188 of the medical device 100, and the second electrical contact 183 may be in electrical communication with the electrical contact 189 of the medical device 100. In some embodiments, one or both of the electrical contacts 188, 189 are leaf spring contacts. The leaf spring contacts 188, 189 may be configured to maintain electrical contact with the contacts 182, 183 of the thermal energy delivery probe 180 as the stylet 181 of the thermal energy delivery probe 180 is displaced relative to the second tubular conductor 140. In other words, electrical communication between the contacts 182, 183 of the thermal energy delivery probe 180 and the contacts 188, 189 may be maintained despite movement of the thermal energy delivery probe 180 relative to the housing 110. Electrical communication between the contacts 182, 183 and the contacts 188, 189 may create an electrical circuit for the delivery of thermal energy to tissue of the patient. The electrical contacts 182, 183 may be raised electrical contacts that are hard wired to the adaptor 184 (e.g., a LEMO style adaptor).

The thermal energy delivery probe 180 may be inserted through the port 123 to vary the position of one or more temperature sensors 158, 159 (e.g., thermocouples) that are attached to or otherwise coupled to the stylet 181 of the thermal energy delivery probe 180. In other words, in some embodiments, the thermal energy delivery probe 180 is displaceable with respect to the second tubular conductor 140, thereby enabling displacement of the one or more temperature sensors 158, 159 relative to the second tubular conductor 140. For example, in some embodiments, the thermal energy delivery probe 180 is inserted such that a temperature sensor 158 is aligned with a protrusion 174 of the on the outer sleeve 170. In some instances, indicia on the port 123 may help a practitioner to determine the position of a temperature sensor.

For example, in some embodiments, when the thermal energy delivery probe 180 is inserted into the port 123 and rotated such that the bottom edge of a hub 185 of the thermal energy delivery probe 180 is aligned with a first indicium 127, a temperature sensor 158 may be disposed a particular distance ($D_1$ of FIG. 20) (e.g., 5 mm) from a center of the exposed portion 132 of the tubular insulator 130. When the bottom edge of the hub 185 is aligned with the second indicium 128, the temperature sensor 158 may be disposed a different distance ($D_2$ of FIG. 20) (e.g., 10 mm) from a center of the exposed portion 132 of the tubular insulator 130. When the bottom edge of the hub 185 is aligned with the third indicium 129, the temperature sensor 158 may be disposed still another distance ($D_3$ of FIG. 20) (e.g., 15 mm) from a center of the exposed tubular insulator 130.

In some embodiments, when the bottom edge of the hub 185 (or some other portion of the thermal energy delivery probe 180) is aligned with an indicium 127, 128, 129 on the port 123, the temperature sensor 158 may be aligned with a protrusion 172, 173, 174 or intrusion (not shown) on the outer sleeve 170, thereby allowing the practitioner to determine the position of the temperature sensor by fluoroscopy. In some embodiments, a second temperature sensor 159 may be disposed proximal of a first temperature sensor 158. For example, a first temperature sensor 158 of the thermal energy delivery probe 180 may be disposed at or adjacent to the distal end of the stylet 181 while a second temperature sensor 159 is disposed proximal of the first temperature sensor 158.

In some embodiments, such as the embodiment depicted in FIG. 20A, instead of one or more protrusions on the outer sleeve 170', the medical device 100' may instead include one or more intrusions 172', 173', 174' or protrusions (not shown) adjacent the distal end of the first tubular conductor 120'. In other words, in some embodiments, one or more protrusions or intrusions 172', 173', 174' are disposed proximal of the insulator 130'. The intrusions 172', 173', 174' or protrusions may be visible by radiography. The medical device 100' may be configured such that a temperature sensor of the thermal energy delivery probe is aligned with an intrusion 172', 173', 174' or protrusion when the bottom edge of the hub (or some other portion of the thermal energy delivery probe) is aligned with an indicium (e.g., an indicium on the port). Aligning a temperature sensor with one of the intrusions 172', 173', 174' may be accomplished in a manner similar to that described above in connection with protrusions 173, 173, 174 on the outer sleeve 170. In some embodiments, protrusions and/or intrusions are disposed on both the outer sleeve and the first tubular conductor. Some embodiments may lack protrusions and/or intrusions on both the outer sleeve and the first tubular conduit.

Once the articulating distal portion 138 of the medical device 100 is properly positioned within the tissue of the vertebra and the one or more temperature sensors 158, 159 are properly positioned within the utility channel 146 of the medical device 100, the medical device 100 may be activated for ablation, thereby causing an electrical current to flow between the distal portion 144 of the second tubular conductor 140 and the first tubular conductor 120 via tissue within the vertebra of the patient. For example, an adaptor 184 of the thermal energy delivery probe 180 may be connected to a power supply (e.g., a radiofrequency generator). An actuator that is in electrical communication with the power supply and/or the thermal energy delivery probe may then be actuated, thereby creating a radiofrequency current that flows through a circuit that includes the thermal energy delivery device 180, the electrical contacts 182, 183, the electrical contacts 188, 189, the wires 117, 118, the first tubular conductor 120, the second tubular conductor 140, and the tissue of the patient. The radiofrequency current may flow from the radiofrequency generator, through the electrical contacts 183, 189, through the wire 118 down the second tubular conductor 140, arching across the exposed portion 132 of the insulator 130 through tissue of the patient to the first tubular conductor 120, through the wire 117, across the contacts 188, 182, and back to the generator. In this manner, radiofrequency energy may be provided between the first tubular conductor 120 and the second tubular conductor 140 via tissue of the patient. Due to the oscillation of the current at radio frequencies, the tissue through which the electrical current travels and/or tissue within the near-field region may be heated. Stated differently, due to the electrical current flowing between the electrodes, ionic agitation occurs, thereby creating friction which heats up nearby tissue. Once the tissue has reached a sufficient temperature (e.g., approximately 50° C., such as between 45° C. and 55° C.) as measured by one or more temperature sensors, such as the temperature sensors 158, 159 on the stylet 181 of the thermal energy delivery probe 180, the medical device 100 may be deactivated, thereby preventing the unintended heating of healthy tissue. Stated differently, one or more thermocouples may be used to actively monitor temperature within the desired ablation region. When radiofrequency energy from the thermal energy delivery device 180 causes the tissue to reach a predetermined (e.g., ablation) temperature, the medical device 100 may be deactivated, thereby restricting ablation to the desired region. In this manner, predictable, measurable, and/or uniform ablation zones may be created in cancerous tissue. In other words, once temperature measurements from the one or more temperature sensors have been obtained, the practitioner may, based on the input from the one or more temperature sensors, (1) alter the location of the distal end 101 of the medical device 100, (2) change the flow rate of electrical current, and/or (3) change the voltage across the electrodes.

If desired, multiple rounds of ablation may be carried out in a single procedure. For example, after a portion of the tissue within a tumor has been ablated using the technique described above, the articulating distal portion 138 of the medical device 100 may be repositioned to a new location within the tumor. Once positioned in this new location, the medical device 100 may be activated to kill tissue in a second region of the tumor. This process may be completed as many times as is necessary to ensure that the entire tumor is adequately treated. Once there is no need or desire for further ablation, the thermal energy delivery probe 180 may be retracted and removed from the port 123 of the medical device 100.

Once the tissue from the tumor has been treated by radiofrequency energy, a bone cement may be delivered to a cavity within the vertebra of the patient, thereby providing stabilization to the vertebra. For example, in some embodiments, the medical device 100 includes a cement delivery cartridge 190 (see FIGS. 22-25) that is configured to facilitate delivery of a bone cement through the utility channel 146 of the medical device 100 and out of a distal opening at the distal end 101 of the second tubular conductor 140. The cement delivery cartridge 190 may include a stylet 191, an elongate tubular distal portion 192, an inflexible hollow portion 193, a proximal adaptor 194 (e.g., a luer connection), and a latch 195.

Figure 23:
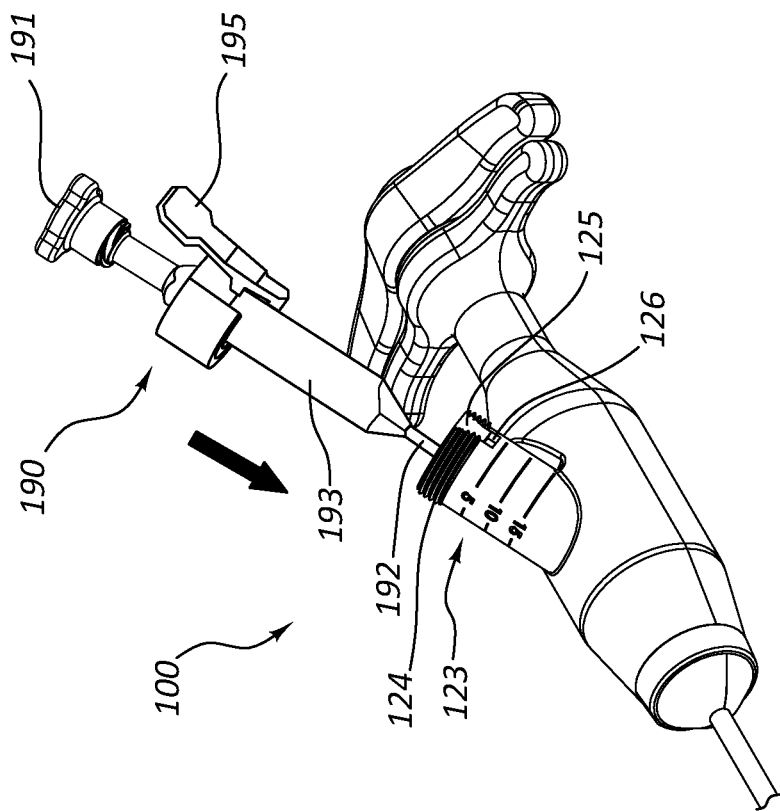
FIG. 23 is a perspective view of the medical device of FIG. 1 showing insertion of the cement delivery cartridge into the port.
Figure 22:
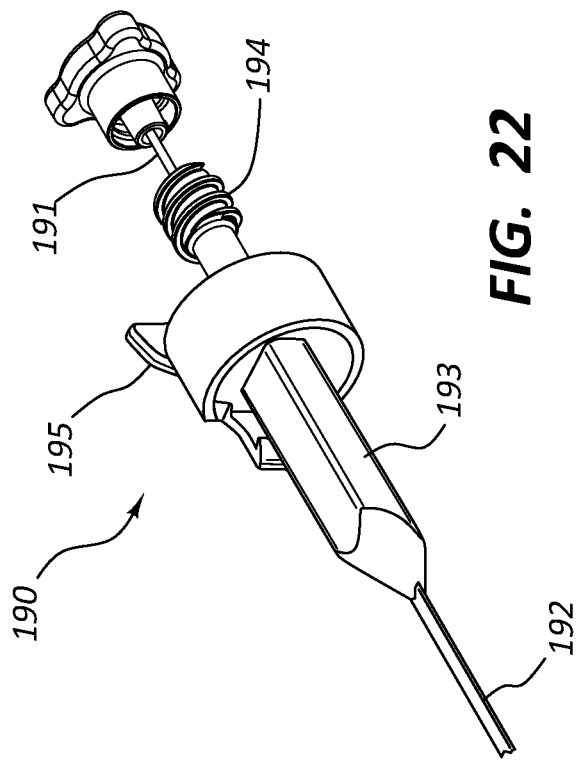
FIG. 22 is a perspective view of a cement delivery cartridge.
Figure 25:
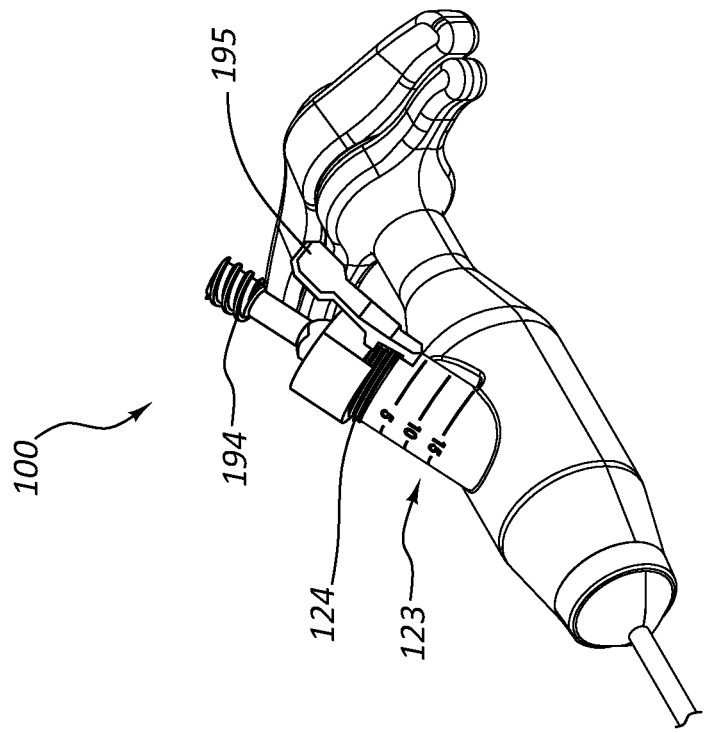
FIG. 25 is a perspective view of the medical device of FIG. 1 showing a fully inserted cement delivery cartridge that is configured to facilitate cement delivery.
Figure 24:
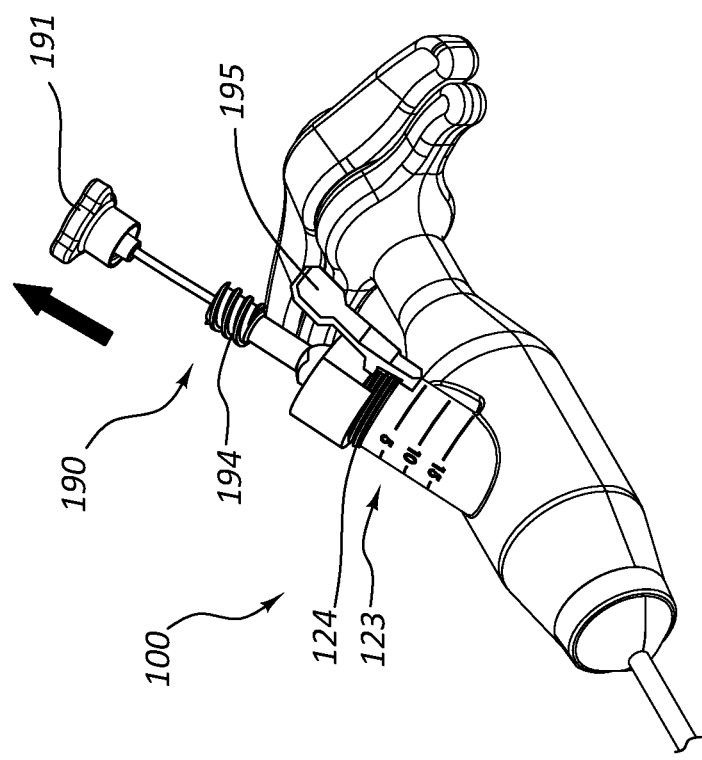
FIG. 24 is a perspective view of the medical device of FIG. 1 showing withdrawal of a stylet of the cement delivery cartridge after the cement delivery cartridge has been fully inserted into the port.

To deliver bone cement to the vertebra of the patient, the distal end of the cement delivery cartridge 190 may be inserted into the port 123 of the medical device 100 as shown in FIG. 23. As the cement delivery cartridge 190 is inserted into the port 123, the stylet 191 of the cement delivery cartridge 190 may be disposed within a channel of the cement delivery cartridge. The stylet 191 may confer increased rigidity to the tubular distal portion 192 of the cement delivery cartridge 190 during insertion into the utility channel 146 of the medical device 100.

In some embodiments, the tubular distal portion 192 of the cement delivery device 190 can be inserted into the utility channel 146 of the medical device 100 only one way due to the geometry of the cement delivery cartridge 190 and the port 123. In some embodiments, the tubular distal portion 192 is flexible, thereby allowing the tubular distal portion 192 to adopt a non-linear path.

As the cement delivery cartridge 190 is inserted into the port 123, a latch 195 on the side of the cement delivery cartridge 190 may slide across a discontinuity 125 in the threads 124 and become seated within a recess 126 in the port 123. In this manner, the latch 195 may lock the cement delivery cartridge 190 to the port 123 without rotation of the cement delivery cartridge 190 relative to the port 123. Once the cement delivery cartridge 190 is locked to the port 123, the stylet 191 may be removed (see FIG. 24).

Once the stylet 191 has been removed (see FIG. 25), the cement delivery cartridge 190 may be coupled to a pump (not shown) that is configured to pump bone cement into a cavity in the vertebra of a patient. For example, the pump may deliver bone cement to the proximal adaptor 194 of the cement delivery cartridge 190 and then advance the bone cement through the cement delivery cartridge 190 into the vertebra of the patient.

In some embodiments, the bone cement comprises methyl methacrylate. In some embodiments, the bone cement is an ultra-high viscosity bone cement with an extended working time. The bone cement, once hardened, may stabilize the vertebra of the patient.

Once the cement has been delivered to the patient, the cement delivery cartridge 190 may be uncoupled from the port 123 of the medical device 100 by pressing the latch 195 toward the adaptor 194 and pulling the cement delivery cartridge 190 out of both the utility channel 146 and the port 123.

Articulation or bending of the distal portion 138 of the medical device 100 may be utilized to position the distal portion 138 of the medical device 100 for delivery of cement via the cement delivery cartridge 190, positioning of the elongate cutting instrument 175 when taking a biopsy, and/or for targeting the area to which thermal energy is delivered and the thermal energy delivery probe 180 is coupled to the medical device 100.

Devices, assemblies and methods within the scope of this disclosure may deviate somewhat from the particular devices and methods discussed above in connection with the medical device 100. For example, in some embodiments, no biopsy sample is obtained during the medical procedure. Stated differently, in some embodiments, no elongate cutting instrument is employed during the medical procedure. In some embodiments, no cement is delivered through a utility channel of a medical device that is also used for ablation. In other words, in some embodiments, cement delivery involves the use of a separate medical device. For example, in some embodiments, one or both of the second tubular conductor and the outer sleeve have sealed distal ends that do not allow for the delivery of cement through the medical device.

Figure 26:
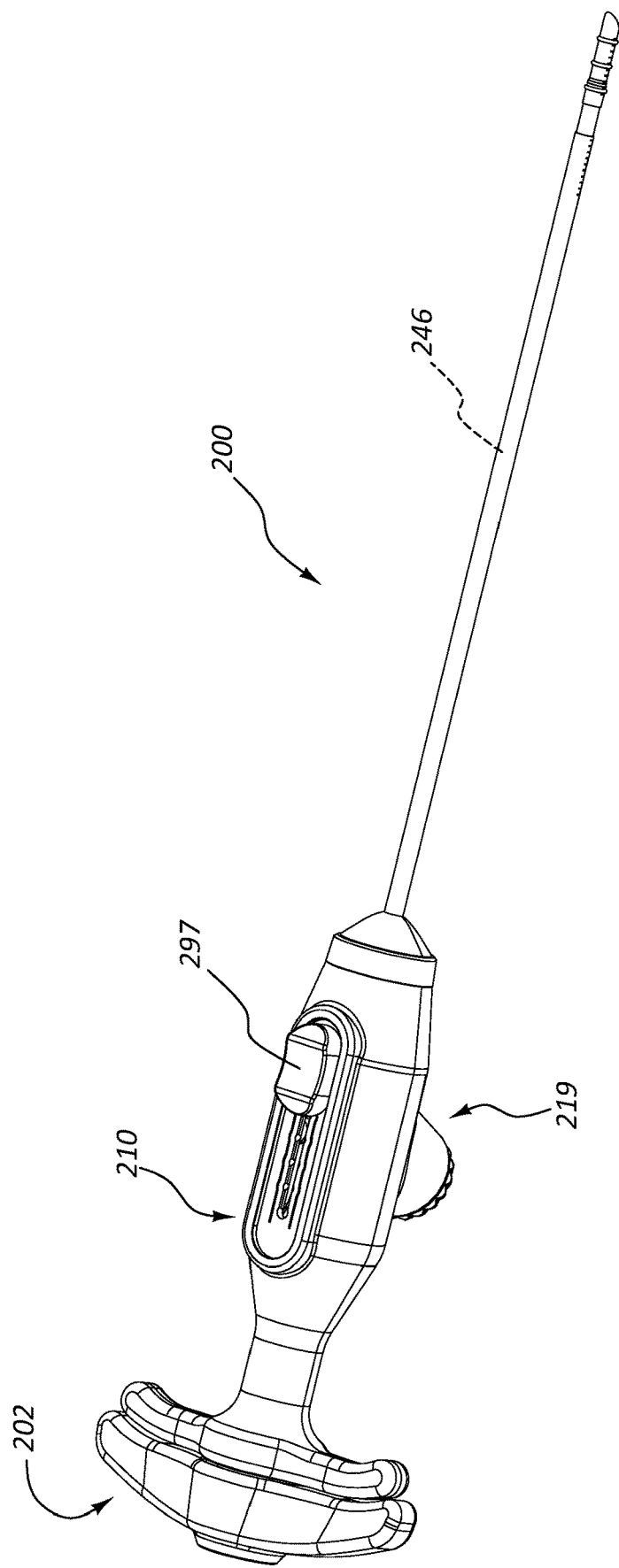
FIG. 26 is a perspective view of a medical device according to another embodiment.
Figure 27:
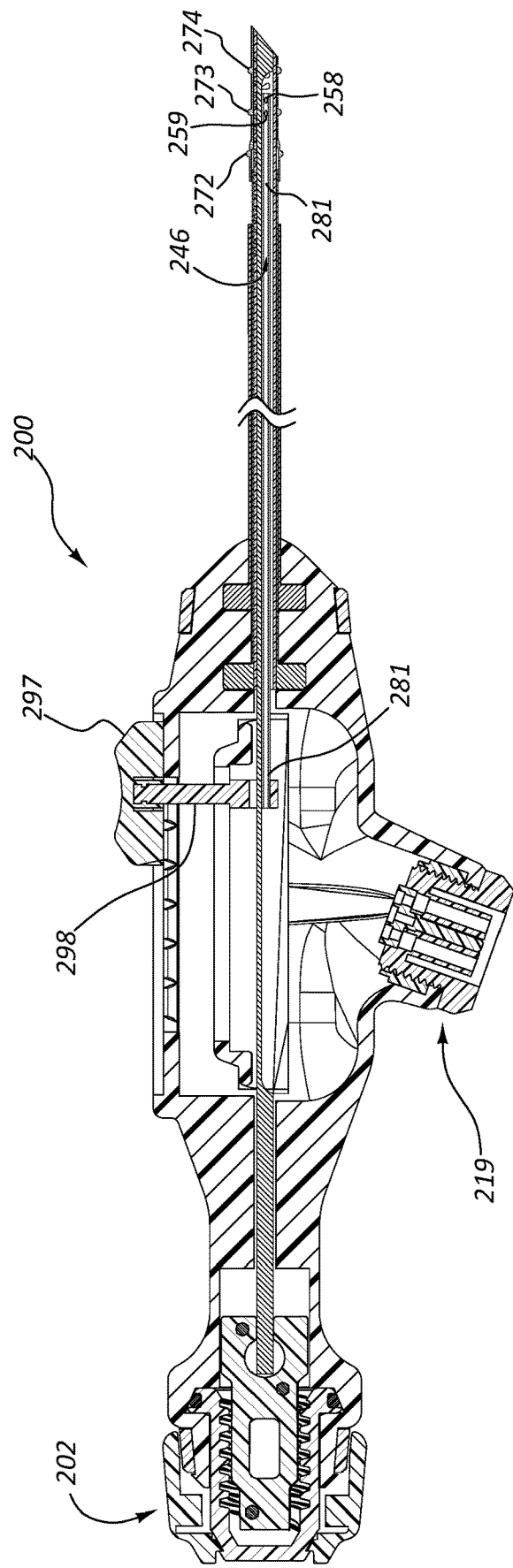
FIG. 27 is a cross-sectional view of the medical device of FIG. 26.

FIGS. 26 and 27 depict an embodiment of a medical device 200 that resembles the medical device 100 described above in certain respects. Accordingly, like features are designated with like reference numerals, with the leading digits incremented to "2." For example, the embodiment depicted in FIGS. 26-27 includes a handle 202 that may, in some respects, resemble the handle 102 of FIGS. 1-25. Relevant disclosure set forth above regarding similarly identified features thus may not be repeated hereafter. Moreover, specific features of the medical device 100 and related components shown in FIGS. 1-25 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the medical device 200 and related components depicted in FIGS. 26 and 27. Any suitable combination of the features, and variations of the same, described with respect to the medical device 100 and related components illustrated in FIGS. 1-25 can be employed with the medical device 200 and related components of FIGS. 26 and 27, and vice versa.

FIG. 26 provides a perspective view of the medical device 200, while FIG. 27 provides a cross-sectional side view of the medical device 200. Like the medical device 100 described above, the medical device 200 is configured to facilitate tumor ablation, but is not designed for the delivery of bone cement to the patient. In other words, in embodiments that use the medical device 200, bone cement is generally delivered using a separate medical device.

More particularly, the medical device 200 includes a side adaptor 219 that is integrated with the housing 210. The adaptor 219 is configured to couple to a power supply that delivers radiofrequency energy to heat and/or kill tissue within the patient.

The medical device 200 further includes a slidable tab 297 that is configured to facilitate placement of one or more temperature sensors 258, 259 within a utility channel 246 of the medical device 200. More particularly, the slidable tab 297 may be coupled to a rod 298 that is coupled to a stylet 281. By sliding the slidable tab 297 in a proximal direction, the stylet 281 may be retracted. Conversely, by sliding the slidable tab 297 in a distal direction, the stylet 281 may be advanced. In this manner, the position of temperature sensors 258, 259 that are attached to the stylet 281 may be controlled. For example, in some embodiments, the housing 210 includes one of more indicia that help a practitioner determine the location of one or more temperature sensors.

For example, when the slidable tab 297 is aligned with a first indicium on the housing 210, a temperature sensor 258 on the stylet 281 may be aligned with a first protrusion 272 on the outer sleeve. When the slidable tab 297 is aligned with a second indicium on the housing 210, the temperature sensor 258 may be aligned with a second protrusion 273 on the outer sleeve. Other indicia may indicate alignment of a temperature sensor 258 with one or more other features or elements of the medical device 200.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A medical device for spinal tumor ablation, the medical device comprising:
   a first tubular conductor;
   a tubular insulator extending through the first tubular conductor;
   a second tubular conductor extending through the tubular insulator such that a distal portion of the second tubular conductor is disposed distal of the insulator;
   an elongate shaft extending through the second tubular conductor, wherein the elongate shaft comprises a distal portion having a semicircular cross-section, wherein the second tubular conductor and the distal portion of the elongate shaft form a utility channel that extends from a proximal opening of the second tubular conductor to a distal opening at a distal end of the second tubular conductor;
   wherein the distal portion of the elongate shaft is coupled to the second tubular conductor, and
   wherein manipulation of the elongate shaft causes articulation of an articulating distal portion of the medical device; and
   a port disposed proximal of the second tubular conductor, wherein the port is configured to provide access to a proximal opening of the utility channel.

2. The medical device of claim 1, wherein the medical device is configured such that, when the medical device is activated for ablation within a vertebra of a patient, an electrical current flows between the distal portion of the second tubular conductor and the first tubular conductor via tissue within the vertebra of the patient.

3. The medical device of claim 1, the articulating distal portion is configured to transition from a linear configuration to a non-linear configuration.

4. The medical device of claim 1, further comprising a thermal energy delivery probe that is configured to be at least partially disposed within the utility channel when the thermal energy delivery probe is fully inserted into the port.

5. The medical device of claim 4, wherein the thermal energy delivery probe is configured to contact one or more electrical contacts of the medical device, thereby creating a circuit for the delivery of thermal energy to tissue of the patient.

6. The medical device of claim 4, wherein:
   the thermal energy delivery probe further comprises a stylet; and
   one or more temperature sensors are attached to the stylet.

7. The medical device of claim 6, wherein the port includes indicia for determining the position of the one or more temperature sensors.

8. The medical device of claim 7, wherein the thermal energy delivery probe comprises threads that are configured to engage with threads on the port, wherein rotation of the thermal energy delivery probe relative to the port causes thread-based displacement of the thermal energy delivery probe relative to the second tubular conductor.

9. The medical device of claim 1, further comprising an elongate cutting instrument for obtaining a biopsy sample, wherein the elongate cutting instrument, when fully inserted into the port, extends through the distal opening at the distal end of the second tubular conductor.

10. The medical device of claim 1, further comprising a cement delivery cartridge, wherein the cement delivery cartridge is configured to facilitate delivery of a cement through the utility channel and out of the distal opening at the distal end of the second tubular conductor.

11. The medical device of claim 1, further comprising a thermal energy delivery probe and a cement delivery cartridge, wherein the medical device is configured to permit sequential insertion of a thermal energy delivery probe into the port, removal of the thermal energy delivery probe from the port, and then insertion of the cement delivery cartridge into the port.

* * * * *